US006607724B2

(12) United States Patent
O'Reilly et al.

(10) Patent No.: US 6,607,724 B2
(45) Date of Patent: Aug. 19, 2003

(54) COMPOSITIONS AND METHODS FOR INHIBITING ANGIOGENESIS

(75) Inventors: Michael S. O'Reilly, Winchester, MA (US); M. Judah Folkman, Brookline, MA (US); Steven Pirie-Shepherd, Waltham, MA (US)

(73) Assignee: Children's Hospital, Boston, MA (US)

( * ) Notice: Subject to any disclaimer, the term of this patent is extended or adjusted under 35 U.S.C. 154(b) by 0 days.

(21) Appl. No.: 09/414,834

(22) Filed: Oct. 8, 1999

(65) Prior Publication Data

US 2002/0076413 A1 Jun. 20, 2002

Related U.S. Application Data

(60) Provisional application No. 60/103,526, filed on Oct. 8, 1998, and provisional application No. 60/116,131, filed on Jan. 15, 1999.

(51) Int. Cl.⁷ ...................... A61K 39/00; A61K 39/385; A01N 37/18

(52) U.S. Cl. ................. 424/184.1; 424/192.1; 424/193.1; 514/2

(58) Field of Search ............ 424/184.1, 192.1, 424/193.1; 514/2

(56) References Cited

U.S. PATENT DOCUMENTS

| | | | |
|---|---|---|---|
| 4,087,415 A | 5/1978 | Bick et al. |
| 4,517,294 A | 5/1985 | Bock et al. |
| 4,632,981 A | 12/1986 | Bock et al. |
| 4,734,279 A | 3/1988 | Stephan et al. |
| 5,151,509 A | 9/1992 | Kotwal et al. |
| 5,319,072 A | 6/1994 | Uemura et al. |
| 5,420,252 A | 5/1995 | Kato et al. |
| 5,589,516 A | 12/1996 | Uriyu et al. |
| 5,618,713 A | 4/1997 | Zettlmeissl et al. |
| 5,700,663 A | 12/1997 | Zettlmeissl et al. |

FOREIGN PATENT DOCUMENTS

WO    WO 99 08522 A    2/1999

OTHER PUBLICATIONS

Burgess et al., J of Cell Bio. 111:2129–2138, 1990.*
Lazar et al. Molecular and Cellular Biology 8:1247–1252, 1988.*
Bowie et al. Science, 247:1306–1310, 1990, p. 1306, col.2.*
Gura (Science, v278, 1997, pp. 1041–1042).*
Zeeter, Annu. Rev. Med., 1998, v49, pp. 407–424.*
Spitler, Cancer Biotherapy, v10(1), 1995, pp. 1–3.*
Reiger et al (Glossary of Genetics and Cytogenetics, Classical and Molecular, 4th Ed., Springer–Verlay, Berlin, 1976).*
Mourery et al., "Anthithrombin III: Structural and Functional Aspects,", Biochimie, 72:599–608 (1990).
Evans et al., "Heparin Binding Site, Conformational Change, and Activation of Antithrombin," Biochemistry, 31:12629–12642 (1992).
Carrell et al., "Mobile Reactive Centre of Serpins and the Control of Thrombosis," Nature, 353:576–578 (1991).
Wardell et al., Biochemistry, 36:13133–13142 (1997).
Pratt et al., "Antithrombin: Structure and Function," Seminars in Hematology, 28, 1:3–9 (1991).
Schreuder et al., "The Intact and Cleaved Human Antithrombin III Complex as a Model for Serpin–proteinase Interactions," Nature Structural Biology, 1:1 (1994).
Zacharski et al., "Occurrence of Blood Coagulation Factors In Situ in Small Cell Carcinoma of the Lung," Cancer, 60:2675–2681 (1987).
Scully et al., "Influence of Tryptophan Modification Upon Digestion of Antithrombin III by Elastase," Thrombosis and Haemostasis, 65 (4):351–354 (1991).
Nishioka et al., "The Role of the COOH–terminal Region of Antithrombin III," The Journal of Biological Chemistry, 267 (31):22224–22229 (1992).
Olson et al., "Effect of Individual Carbohydrate Chains of Recombinant Antithrombin on Heparin Affinity and on the Generation of Glycoforms Differing in Heparin Affinity," Archives of Biochemistry and Biophysics, 341 (2):212–221 (1997).
Mourey et al., "Crystal Structure of Cleaved Bovine Antithrombin III at 3.2 Å Resolution," J. Mol. Biol., 232:223–241 (1993).
Akiyama et al., "Antithrombin III Producing Hepatocellular Carcinoma," Thrombosis Research, 72:193–201 (1993).
O'Reilly et al., "Angiostatin: A Novel Angiogenesis Inhibitor That Mediates the Supression of Metastases by a Lewis Lung Carcinoma," Cell, 79:315–328 (1994).
Carrell, R. W. "How Serpins are Shaping Up," Science, 285:1861–1863 (1999).
Carrell, R. W. et al., "Correction to: Mobile Reactive Centre of Serpins and the Control of Thrombosis," Nature, 364:737–739 (1993).

(List continued on next page.)

Primary Examiner—Anthony C. Capura
Assistant Examiner—Gary B. Nickol
(74) Attorney, Agent, or Firm—Finnegan, Henderson, Farabow, Garrett & Dunner, LLP

(57) ABSTRACT

The invention provides for methods of reducing or inhibiting angiogenesis, tumor growth and endothelial cell proliferation by the administration of compositions containing fragments, conformations, biological equivalent, or derivatives of antithrombin III. The invention also provides for pharmaceutical compositions comprising a fragment, conformation, biological equivalent, or derivative of antithrombin III and methods of identifying novel inhibitors of tumor growth, endothelial cell proliferation, and/or angiogenesis. The invention also relates to compositions and methods for altering angiogenesis in a mammal, as well as to methods of treatment for disorders associated with angiogenesis (e.g., cancer).

7 Claims, 11 Drawing Sheets

OTHER PUBLICATIONS

Figure 1A:
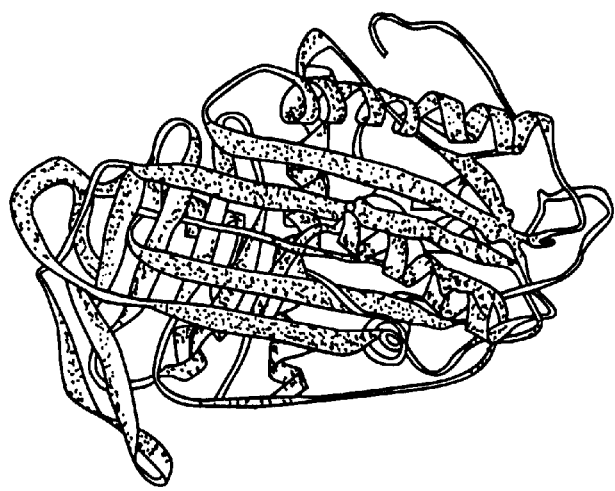
Figure 1A:
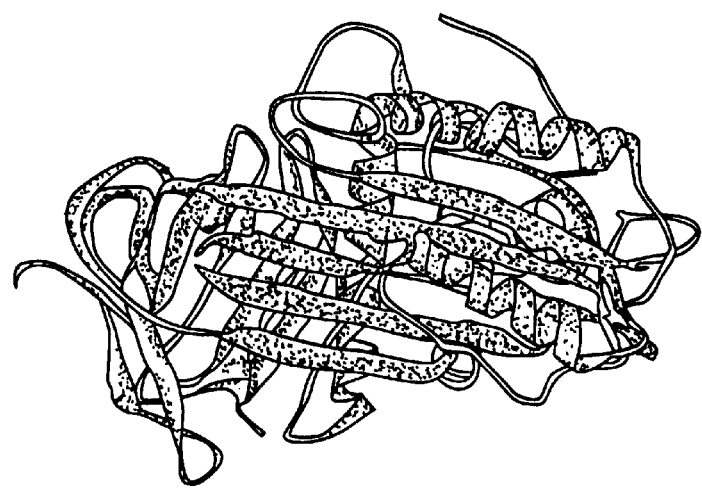
Figure 1A:
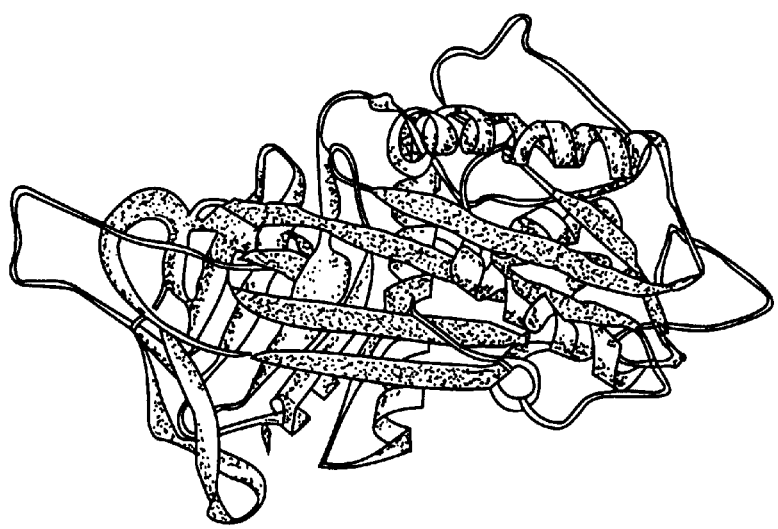

Soff et al., "PAI–1 Expression Human Prostate Carcinoma Cells Inhibits Primary Tumor Growth, Tumor–Associated Angiogenesis and Metastases in an Athymic Mouse Carcinoma Model," *Proc. Eighty–Sixth Ann. Mtgng. Am. Assoc. Cancer Rsrch*, 36: abstract (Mar. 1995).

Tsopanoglou et al., "Thrombin Promotes Angiogenesis by a Mechanism Independent of Fibrin Formation," *Am. J. Physiology*, 264: abstract (1993).

O'Reilly et. al., "Antiangiogenic Activity of the Cleaved Conformation of the Serpin Antithrombin," *Science*, 285:1926–1928 (1999).

Dawson et al., "Pigment Epithelium–Derived Factor: A Potent Inhibitor of Angiogenesis," *Science*, 285: 245–248 (1999).

* cited by examiner

SEQ:ID NO. 1

ACT_SITE  425  426  REACTIVE BOND.

IN ONE-LETTER CODE:

```
        1           11          21          31          41          51
  1  MYSNVIGTVT  SGKRKVYLLS  LLLIGFWDCV  TCHGSPVDIC  TAKPRDIPMN  PMCIYRSPEK   60
 61  KATEDEGSEQ  KIPEATNRRV  WELSKANSRF  ATTFYQHLAD  SKNDNDNIFL  SPLSISTAFA  120
121  MTKLGACNDT  LQQLMEVFKF  DTISEKTSDQ  IHFFFAKLNC  RLYRKANKSS  KLVSANRLFG  180
181  DKSLTFNETY  QDISELVYGA  KLQPLDFKEN  AEQSRAAINK  WVSNKTEGRI  TDVIPSEAIN  240
241  ELTVLVLVNT  IYFKGLWKSK  FSPENTRKEL  FYKADGESCS  ASMMYQEGKF  RYRRVAEGTQ  300
301  VLELPFKGDD  ITMVLILPKP  EKSLAKVEKE  LTPEVLQEWL  DELEEMLVV   HMPRFRIEDG  360
361  FSLKEQLQDM  GLVDLFSPEK  SKLPGIVAEG  RDDLYVSDAF  HKAFLEVNEE  GSEAAASTAV  420
421  VIAGRSLNPN  RVTFKANRPF  LVFIREVPLN  TIIFMGRVAN  PCVK                    
```

FIG. 1b

IN THREE-LETTER CODE:

```
       1   2   3   4   5   6   7   8   9   10  11  12  13  14  15
  1  Met Tyr Ser Asn Val Ile Gly Thr Val Thr Ser Gly Lys Arg Lys  15
 16  Val Tyr Leu Leu Ser Leu Leu Leu Ile Gly Phe Trp Asp Cys Val  30
 31  Thr Cys His Gly Ser Pro Val Asp Ile Cys Thr Ala Lys Pro Arg  45
 46  Asp Ile Pro Met Asn Pro Met Cys Ile Tyr Arg Ser Pro Glu Lys  60
 61  Lys Ala Thr Glu Asp Glu Gly Ser Glu Gln Lys Ile Pro Glu Ala  75
 76  Thr Asn Arg Arg Val Trp Glu Leu Ser Lys Ala Asn Ser Arg Phe  90
 91  Ala Thr Thr Phe Tyr Gln His Leu Ala Asp Ser Lys Asn Asp Asn 105
106  Asp Asn Ile Phe Leu Ser Pro Leu Ser Ile Ser Thr Ala Phe Ala 120
121  Met Thr Lys Leu Gly Ala Cys Asn Asp Thr Leu Gln Gln Leu Met 135
136  Glu Val Phe Lys Phe Asp Thr Ile Ser Glu Lys Thr Ser Asp Gln 150
151  Ile His Phe Phe Phe Ala Lys Leu Asn Cys Arg Leu Tyr Arg Lys 165
166  Ala Asn Lys Ser Ser Lys Leu Val Ser Ala Asn Arg Leu Phe Gly 180
181  Asp Lys Ser Leu Thr Phe Asn Glu Thr Tyr Gln Asp Ile Ser Glu 195
196  Leu Val Tyr Gly Ala Lys Leu Gln Pro Leu Asp Phe Lys Glu Asn 210
211  Ala Glu Gln Ser Arg Ala Ala Ile Asn Lys Trp Val Ser Asn Lys 225
226  Thr Glu Gly Arg Ile Thr Asp Val Ile Pro Ser Glu Ala Ile Asn 240
241  Glu Leu Thr Val Leu Val Leu Val Asn Thr Ile Tyr Phe Lys Gly 255
256  Leu Trp Lys Ser Lys Phe Ser Pro Glu Asn Thr Arg Lys Glu Leu 270
271  Phe Tyr Lys Ala Asp Gly Glu Ser Cys Ser Ala Ser Met Met Tyr 285
286  Gln Glu Gly Lys Phe Arg Tyr Arg Arg Val Ala Glu Gly Thr Gln 300
301  Val Leu Glu Leu Pro Phe Lys Gly Asp Asp Ile Thr Met Val Leu 315
316  Ile Leu Pro Lys Pro Glu Lys Ser Leu Ala Lys Val Glu Lys Glu 330
331  Leu Thr Pro Glu Val Leu Gln Glu Trp Leu Asp Glu Leu Glu Glu 345
346  Met Met Leu Val Val His Met Pro Arg Phe Arg Ile Glu Asp Gly 360
361  Phe Ser Leu Lys Glu Gln Leu Gln Asp Met Gly Leu Val Asp Leu 375
376  Phe Ser Pro Glu Lys Ser Lys Leu Pro Gly Ile Val Ala Glu Gly 390
391  Arg Asp Asp Leu Tyr Val Ser Asp Ala Phe His Lys Ala Phe Leu 405
406  Glu Val Asn Glu Glu Gly Ser Glu Ala Ala Ala Ser Thr Ala Val 420
421  Val Ile Ala Gly Arg Ser Leu Asn Pro Asn Arg Val Thr Phe Lys 435
436  Ala Asn Arg Pro Phe Leu Val Phe Ile Arg Glu Val Pro Leu Asn 450
451  Thr Ile Ile Phe Met Gly Arg Val Ala Asn Pro Cys Val Lys
```

FIG. 1b cont.

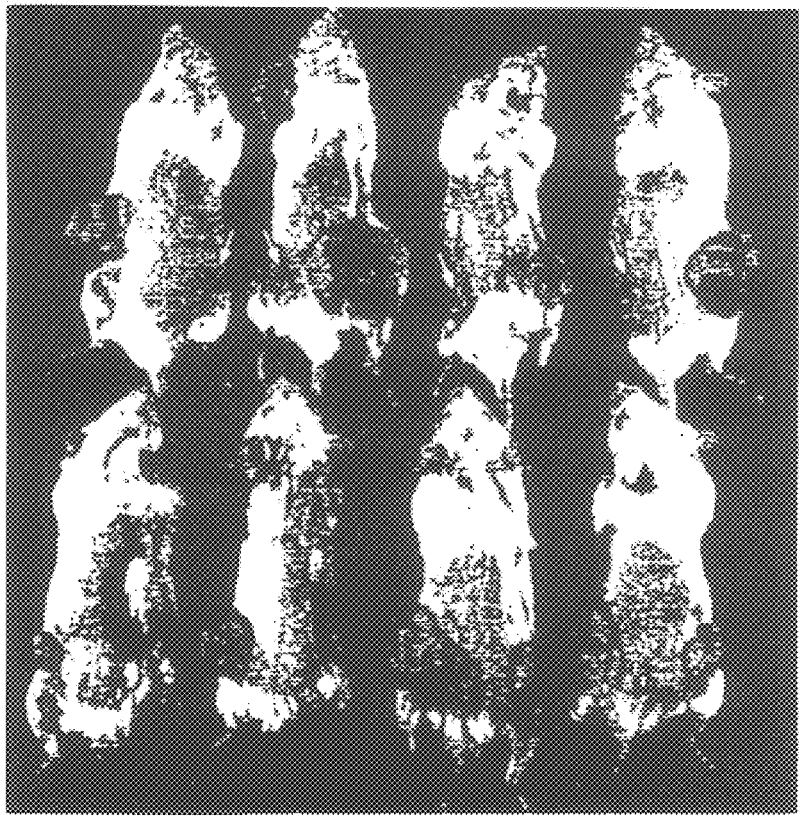
FIG. 7(a) NCI-H69i TUMOUR
FIG. 7(b) NCI-H69ni TUMOUR

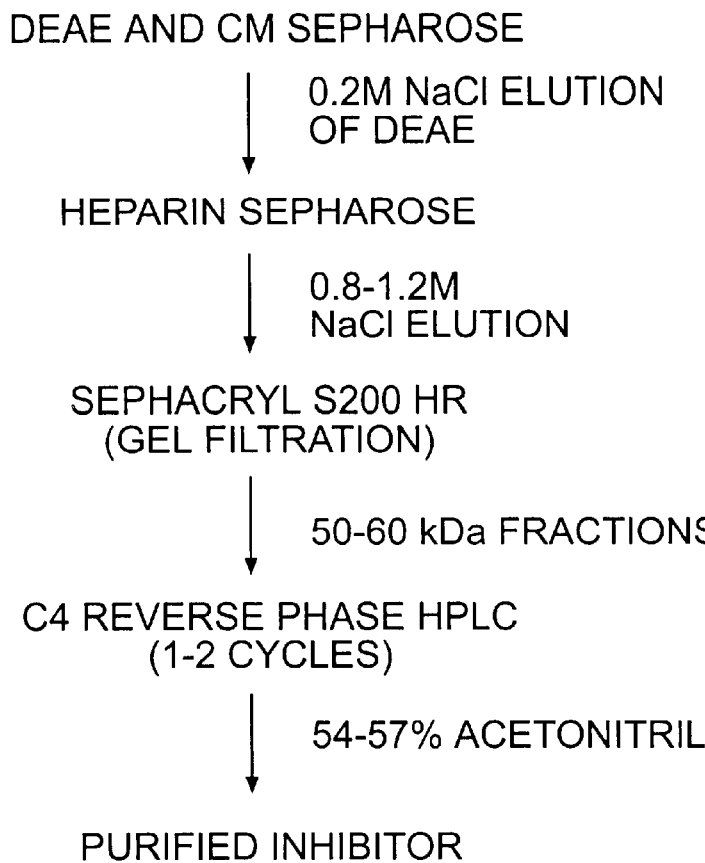
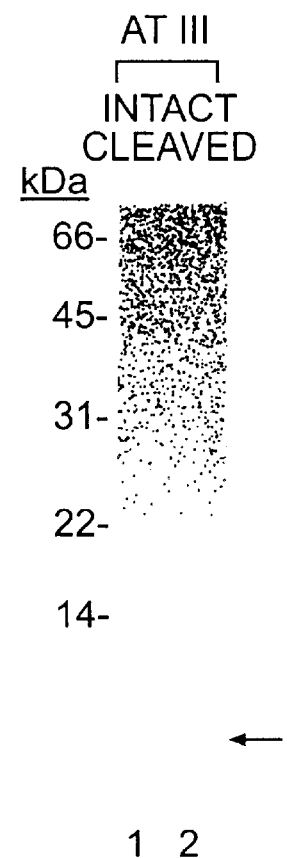
FIG. 8(a)      FIG. 8(b)

SEQUENCE LISTING

<160> NUMBER OF SEQ ID NOS: 1

<210> SEQ ID NO 1
<211> LENGTH: 464
<212> TYPE: PRT
<213> ORGANISM: Homo sapiens
<220> FEATURE:
<223> OTHER INFORMATION: Antithrombin III

<400> SEQUENCE: 1

```
Met Tyr Ser Asn Val Ile Gly Thr Val Thr Ser Gly Lys Arg Lys Val
  1               5                  10                  15

Tyr Leu Ser Leu Leu Leu Ile Gly Phe Trp Asp Cys Val Thr Cys
             20                  25                  30

His Gly Ser Pro Val Asp Ile Cys Thr Ala Lys Pro Arg Asp Ile Pro
             35                  40                  45

Met Asn Pro Met Cys Ile Tyr Arg Ser Pro Glu Lys Lys Ala Thr Glu
         50                  55                  60

Asp Glu Gly Ser Glu Gln Lys Ile Pro Glu Ala Thr Asn Arg Arg Val
 65                  70                  75                  80

Trp Glu Leu Ser Lys Ala Asn Ser Arg Phe Ala Thr Thr Phe Tyr Gln
                 85                  90                  95

His Leu Ala Asp Ser Lys Asn Asp Asn Asp Asn Ile Phe Leu Ser Pro
            100                 105                 110

Leu Ser Ile Ser Thr Ala Phe Ala Met Thr Lys Leu Gly Ala Cys Asn
        115                 120                 125

Asp Thr Leu Gln Gln Leu Met Glu Val Phe Lys Phe Asp Thr Ile Ser
    130                 135                 140

Glu Lys Thr Ser Asp Gln Ile His Phe Phe Phe Ala Lys Leu Asn Cys
145                 150                 155                 160

Arg Leu Tyr Arg Lys Ala Asn Lys Ser Ser Lys Leu Val Ser Ala Asn
                165                 170                 175

Arg Leu Phe Gly Asp Lys Ser Leu Thr Phe Asn Glu Thr Tyr Gln Asp
            180                 185                 190

Ile Ser Glu Leu Val Tyr Gly Ala Lys Leu Gln Pro Leu Asp Phe Lys
        195                 200                 205

Glu Asn Ala Glu Gln Ser Arg Ala Ala Ile Asn Lys Trp Val Ser Asn
    210                 215                 220

Lys Thr Glu Gly Arg Ile Thr Asp Val Ile Pro Ser Glu Ala Ile Asn
225                 230                 235                 240

Glu Leu Thr Val Leu Val Leu Val Asn Thr Ile Tyr Phe Lys Gly Leu
                245                 250                 255

Trp Lys Ser Lys Phe Ser Pro Glu Asn Thr Arg Lys Glu Leu Phe Tyr
            260                 265                 270

Lys Ala Asp Gly Glu Ser Cys Ser Ala Ser Met Met Tyr Gln Glu Gly
        275                 280                 285

Lys Phe Arg Tyr Arg Arg Val Ala Glu Gly Thr Gln Val Leu Glu Leu
    290                 295                 300

Pro Phe Lys Gly Asp Asp Ile Thr Met Val Leu Ile Leu Pro Lys Pro
305                 310                 315                 320
```

```
Glu Lys Ser Leu Ala Lys Val Glu Lys Glu Leu Thr Pro Glu Val Leu
                325                 330                 335
Gln Glu Trp Leu Asp Glu Leu Glu Glu Met Met Leu Val Val His Met
            340                 345                 350
Pro Arg Phe Arg Ile Glu Asp Gly Phe Ser Leu Lys Glu Gln Leu Gln
        355                 360                 365
Asp Met Gly Leu Val Asp Leu Phe Ser Pro Glu Lys Ser Lys Leu Pro
    370                 375                 380
Gly Ile Val Ala Glu Gly Arg Asp Asp Leu Tyr Val Ser Asp Ala Phe
385                 390                 395                 400
His Lys Ala Phe Leu Glu Val Asn Glu Glu Gly Ser Glu Ala Ala Ala
            405                 410                 415
Ser Thr Ala Val Val Ile Ala Gly Arg Ser Leu Asn Pro Asn Arg Val
            420                 425                 430
Thr Phe Lys Ala Asn Arg Pro Phe Leu Val Phe Ile Arg Glu Val Pro
            435                 440                 445
Leu Asn Thr Ile Ile Phe Met Gly Arg Val Ala Asn Pro Cys Val Lys
    450                 455                 460
```

COMPOSITIONS AND METHODS FOR INHIBITING ANGIOGENESIS

This application claims benefit of U.S. Provisional Applications Ser. Nos. 60/103,526 filed Oct. 8, 1998 and 60/116,131 filed Jan. 15, 1999, the disclosures of which are hereby incorporated by reference.

The invention was supported, in whole or in part, by grant CA45548 from the National Institutes of Health. The Government has certain rights in the invention.

Blood vessels are constructed by two processes: vasculogenesis, whereby a primitive vascular network is established during embryogenesis from multipotential mesenchymal progenitors; and angiogenesis, in which preexisting vessels send out capillary sprouts to produce new vessels. Endothelial cells are centrally involved in each process. They migrate, proliferate and then assemble into tubes with tight cell-cell connections to contain the blood (Hanahan, *Science* 277:48–50 (1997)). Angiogenesis occurs when enzymes, released by endothelial cells, and leukocytes begin to erode the basement membrane, which surrounds the endothelial cells, allowing the endothelial cells to protrude through the membrane. These endothelial cells then begin to migrate in response to angiogenic stimuli, forming off-shoots of the blood vessels, and continue to proliferate until the off-shoots merge with each other to form the new vessels.

Normally angiogenesis occurs in humans and animals in a very limited set of circumstances, such as embryonic development, wound healing, and formation of the corpus luteum, endometrium and placenta. However, aberrant angiogenesis is associated with a number of disorders, including, tumor metastasis. In fact, it is commonly believed that tumor growth is dependent upon angiogenic processes. Thus, the ability to increase or decrease angiogenesis has significant implications for clinical situations, such as wound healing (e.g., graft survival) or cancer therapy, respectively.

Antithrombin or Antithrombin III (AT3) is a single chain glycoprotein involved in the coagulation process. It is synthesized primarily in the liver with a signal peptide of 32 amino acids necessary for its intracellular transport through the endoplasmic reticulum; the peptide is then cleaved prior to secretion. Mourey et al., *Biochimie* 72:599–608 (1990).

AT3 is a member of the serpin family of proteins and functions as an inhibitor of thrombin and other enzymes involved in the clotting cascade. As used herein, the active native intact form of AT3 is designated the S (stressed) form (S-AT3). S-AT3 forms a tight binding complex with thrombin (markedly enhanced by the presence of heparin) and other enzymes (not all serpins have heparin affinity).

S-AT3 can be cleaved to the relaxed (R)-conformation (R-AT3) by a variety of enzymes, including thrombin. Evans et al., *Biochemistry* 31:1262912642 (1992). For example, it has been thought that thrombin binds to a reactive C-terminal loop of AT3 and the resultant complex slowly dissociates releasing thrombin and cleaving off the C-terminal loop of inactive AT3, resulting in R-AT3. R-AT3 is unable to bind thrombin and has a conformation that is quite different from that of S-AT3. The role of R-AT3 had only been known to facilitate hepatic clearance of the molecule.

Other forms of AT3, such as L-AT3, which is the group of forms of ATIII that includes both the latent form and the locked form, are similar in conformation to R-AT3, and are also known in the art. Carrell et al., *Nature* 353, 576–578 (1991); Wardell et al., *Biochemistry* 36, 13133–13142 (1997). L-AT3, for example, can be produced by limited denaturing and renaturing the AT3 protein under specific temperature conditions, e.g., with guanidium chloride.

Prior to the present invention, AT3 was not known to be associated with angiogenesis. The present invention is, in one embodiment, drawn to a fragment, conformation, derivative or biological equivalent of AT3 that inhibits endothelial cell proliferation, angiogenesis and/or tumor growth in vivo.

In one embodiment, the invention relates to a method of inhibiting tumor growth by delivering or administering a composition comprising a fragment, conformation, biological equivalent, or derivative of AT3. In a preferred embodiment, the fragment, conformation, biological equivalent, or derivative of AT3 is chosen from the L form of AT3, the R form of AT3 and fragments that include the active sites of the L form of AT3 and/or the R form of AT3. The fragment, conformation, biological equivalent, or derivative of AT3 may also be chosen from a synthesized fragment of AT3 that inhibits tumor growth, conformational variations of other serpins that inhibit tumor growth, an aggregate form of AT3 that inhibits tumor growth, or a fusion protein of AT3 that inhibits tumor growth. The composition may further comprise a physiologically acceptable vehicle.

The invention further relates to a method of inhibiting endothelial cell proliferation comprising delivering or administering a composition comprising a fragment, conformation, biological equivalent, or derivative of AT3. In a preferred embodiment, the fragment, conformation, biological equivalent, or derivative of AT3 is chosen from the L form of AT3, the R form of AT3 and fragments that include the active sites of the L form of AT3 and/or the R form of AT3. The fragment, conformation, biological equivalent, or derivative of AT3 may also be chosen from a synthesized fragment of AT3 that inhibits endothelial cell proliferation, conformational variations of other serpins that inhibit endothelial cell proliferation, an aggregate form of AT3 that inhibits endothelial cell proliferation, or a fusion protein of AT3 that inhibits endothelial cell proliferation. The composition may further comprise a physiologically acceptable vehicle.

The invention also relates to a method of reducing or inhibiting angiogenesis comprising delivering or administering a composition comprising a fragment, conformation, biological equivalent, or derivative of AT3. In a preferred embodiment, the fragment, conformation, biological equivalent, or derivative of AT3 is chosen from the L form of AT3, the R form of AT3 and fragments that include the active sites of the L form of AT3 and/or the R form of AT3. The fragment, conformation, biological equivalent, or derivative of AT3 may also be chosen from a synthesized fragment of AT3 that reduces angiogenesis, conformational variations of other serpins that reduce angiogenesis, an aggregate form of AT3 that reduces angiogenesis, or a fusion protein of AT3 that reduces angiogenesis. The composition may further comprise a physiologically acceptable vehicle.

In another embodiment, the invention pertains to a method for identifying an inhibitor of tumor growth or an agent that reduces tumor growth, comprising the steps of inoculating an animal with an appropriate innoculum of tumor cells in each of two suitable inoculation sites; identifying inhibition of growth of a tumor, known as the subordinate tumor, at one inoculation site with concomitant growth of a tumor, known as the dominant tumor, at the other inoculation site; isolating cells from the dominant tumor; and purifying a component which inhibits endothelial cell proliferation and/or angiogenesis from the isolated cells. For example, the component may be purified from conditioned media from the cells. In one embodiment of the invention, the tumor cells are derived from tumors selected from the group consisting of small cell lung cancers and hepatocellular carcinomas. In a particular embodiment, the inoculation sites are the flanks of the animal. In one embodiment the inhibitor of tumor growth is an inhibitor of endothelial cell proliferation. In another embodiment the inhibitor of tumor growth is an inhibitor of angiogenesis. In a further embodiment of the invention, the method further comprises a step of selecting for an animal in which inhibition of the growth of the subordinate tumor by the dominant tumor is substantially complete.

The invention further relates to a method of inhibiting tumor growth comprising delivering or administering an inhibitor of tumor growth identified by the methods described herein to a mammal. In a preferred embodiment the inhibitor of tumor growth is a fragment, conformation, biological equivalent, or derivative of AT3.

It is also within the practice of the invention to use a similar method to identify an agent that reduces or an inhibitor of angiogenesis and/or endothelial cell proliferation. Such a method would also comprise the steps of inoculating an animal with an appropriate inoculum of tumor cells in each of two suitable inoculation sites; identifying inhibition of growth of a tumor, known as the subordinate tumor, at one inoculation site with concomitant growth of a tumor, known as the dominant tumor, at the other inoculation site; isolating cells from the dominant tumor; and purifying a component which inhibits endothelial cell proliferation and/or angiogenesis from the isolated cells. The component may be purified from conditioned media from the cells and in a particular embodiment, the inoculation sites are the flanks of the animal.

The invention further relates to a method of reducing or inhibiting angiogenesis and/or endothelial cell proliferation comprising delivering or administering an inhibitor of angiogenesis and/or endothelial cell proliferation identified by the methods described herein to a mammal. In a preferred embodiment the inhibitor of angiogenesis and/or endothelial cell proliferation is a fragment, conformation, biological equivalent, or derivative of AT3.

The invention also relates to a method of treating a disorder mediated by angiogenesis comprising delivering or administering a composition comprising a fragment, conformation, biological equivalent, or derivative of AT3 in an amount effective to reduce angiogenesis to a mammal. In a preferred embodiment the fragment, conformation, biological equivalent, or derivative of AT3 is chosen from the L form of AT3, the R form of AT3 and fragments that include the active sites of the L form of AT3 and/or the R form of AT3. The fragment, conformation, biological equivalent, or derivative of AT3 may also be chosen from a synthesized fragment of AT3 that reduces angiogenesis, conformational variations of other serpins that reduce angiogenesis, an aggregate form of AT3 that reduces angiogenesis, or a fusion protein of AT3 that reduces angiogenesis. The composition may further comprise a physiologically acceptable vehicle.

The invention also relates to a method of treating a disorder mediated by endothelial cell proliferation comprising delivering or administering a composition comprising a fragment, conformation, biological equivalent, or derivative of AT3 in an amount effective to inhibit endothelial cell proliferation to a mammal. In a preferred embodiment the fragment, conformation, biological equivalent, or derivative of AT3 is chosen from the L form of AT3, the R form of AT3 and fragments that include the active sites of the L form of AT3 and/or the R form of AT3. The fragment, conformation, biological equivalent, or derivative of AT3 may also be chosen from a synthesized fragment of AT3 that inhibits endothelial cell proliferation, conformational variations of other serpins that inhibit endothelial cell proliferation, an aggregate form of AT3 that inhibits endothelial cell proliferation, or a fusion protein of AT3 that inhibits endothelial cell proliferation. The composition may further comprise a physiologically acceptable vehicle.

The invention also relates to a method of enhancing angiogenesis comprising delivering or administering a composition comprising an effective amount of an antagonist of a fragment, conformation, biological equivalent, or derivative of AT3 wherein the fragment, conformation, biological equivalent, or derivative of AT3 reduces angiogenesis to a mammal. This method can be used, for example, in wound healing and assisted reproduction techniques as well as in coronary artery surgery and the revascularization/ collateralization of peripheral vascular vessels. The composition may further comprise a physiologically acceptable vehicle.

The invention also relates to a method of enhancing endothelial cell proliferation comprising delivering or administering a composition comprising an effective amount of an antagonist of a fragment, conformation, biological equivalent, or derivative of AT3 wherein the fragment, conformation, biological equivalent, or derivative of AT3 inhibits endothelial cell proliferation to a mammal. The composition may further comprise a physiologically acceptable vehicle.

Another embodiment of the invention is a kit for detecting the presence of a fragment, conformation, biological equivalent, or derivative of AT3. The kit may contain primary reagents suitable for detecting the presence of the fragment, conformation, biological equivalent, or derivative of AT3 and optional secondary agents suitable for detecting the binding of the primary reagent to the fragment, conformation, biological equivalent, or derivative of AT3. In a preferred embodiment, the fragment, conformation, biological equivalent, or derivative of AT3 is the L form of bovine AT3, the R form of bovine AT3, the L form of human AT3, or the R form of human AT3.

The invention provides for direct administration of the fragment, conformation, biological equivalent, or derivative of AT3, along with the use of the fragment, conformation, biological equivalent, or derivative of AT3 with or without physiologically acceptable vehicles, including but not limited to viral vectors including adenoviruses, lipids and any other methods that have been employed in the art to effectuate delivery of biologically active molecules.

The invention also provides for the production of a fragment, conformation, biological equivalent, or derivative of AT3 in vivo by the delivery of an enzyme. It is also within the practice of the invention to produce a fragment, conformation, biological equivalent, or derivative of AT3 in vivo by the delivery of a composition that effectuates a conformational change in a serpin.

The invention also relates to pharmaceutical compositions comprising a fragment, conformation, biological equivalent, or derivative of AT3. The composition may be effective for inhibiting tumor growth, angiogenesis, and/or endothelial cell proliferation. In one embodiment, an anti-angiogenic pharmaceutical composition comprises a purified form of AT3 that reduces angiogenesis. In a preferred embodiment the purified form of AT3 is the L form or R form of AT3 or a fragment or sequence which includes the active site or region of the L form or R form of AT3. The composition may further comprise a physiologically acceptable vehicle. The fragment, conformation, biological equivalent, or derivative of AT3 may be an active ingredient in a pharmaceutical composition that includes carriers, fillers, extenders, dispersants, creams, gels, solutions and other excipients that are common in the pharmaceutical formulatory arts.

The invention also provides for a method of delivering or administering a composition comprising a fragment, conformation, biological equivalent, or derivative of AT3 by any methods that have been employed in the art to effectuate delivery of biologically active molecules, including but not limited to, administration of an aerosolized solution, intravenous injection, orally, parenterally, topically, or transmucosally.

The invention also provides for a pharmaceutical composition that comprises compositions to facilitate delivery of therapeutically effective amounts of the fragment, conformation, biological equivalent, or derivative of AT3. The pharmaceutical compositions of the invention may be formulated to contain one or more additional physiologically acceptable substances that stabilize the compositions for storage and/or contribute to the successful delivery of the fragment, conformation, biological equivalent, or derivative of AT3.

Additional features and advantages of the invention will be set forth in the description which follows, and, in part, will be apparent from the description, or may be learned by the practice of the invention. The objectives and other advantages of the invention will be realized and attained by the compounds and methods particularly pointed out in the written description and claims hereof as well as the appended drawings.

BRIEF DESCRIPTION OF THE DRAWINGS

FIG. 1*a*. shows three conformations of AT3. *b*. (SEQ ID NO: 1) shows the amino acid sequence of human AT3 and the pancreatic elastase cleavage site of the c-terminal reactive loop.

FIG. 2 shows the sequence data and schematic of bovine AT3 and aaAT3. N-terminal sequences were determined by automated Edman degradation on a PE/ABD Procise 494cLC protein sequencer (Foster City, Calif.) with high sensitivity phenylthiohydantoin amino acid detection by capillary HPLC. Sequence library searches and alignments were performed against combined GenBank, Brookhaven Protein, SWISS-PROT, and PIR databases.

FIG. 3 is a graph showing the effects of intact (S), cleaved (R) and (L) conformations of bovine AT3 on capillary endothelial cell proliferation.

FIG. 4 is a graph showing the effects of intact (S), cleaved (R) and (L) conformations of human AT3 on capillary endothelial cell proliferation.

FIG. 5 *a*. is a graph showing the results of treatment with human S-AT3, human R-AT3, human L-AT3 and bovine R-AT3 in mice implanted with a human neuroblastoma. The mean tumor volume and standard error for mice (n=4/group) is shown. Tumor volume was determined using the formula $width^2 \times length \times 0.52$. The experiment was terminated and mice sacrificed and autopsied when control mice began to die or experience morbidity. *b*. Photograph of representative mice from each group on the $12^{th}$ day of treatment. Arrows indicate tumors that have partially regressed.

FIG. 6 shows the treatment of human neuroblastoma with latent or locked human antithrombin III. Mean tumor volume and standard error (n=5/group).

FIG. 7 depicts a model of concomitant resistance. *a*. By selective in vivo passage, a variant of NCI-H69; small cell lung cancer was developed in which a primary flank tumor completely suppresses the growth of a second implant on the opposite flank (arrows). *b*. In another variant of the small cell lung cancer line that does not produce aaAT3, no evidence of concomitant resistance is observed.

FIG. 8 Purification of aaAT3 from the conditioned media of NCI-H69i spheroids. *a*. Purification scheme. *b*. SDS-PAGE (reduced) of intact AT3 (lane 1) and aaAT3 (lane 2) purified from H69i conditioned media. The B-chain of the cleaved form is indicated with an arrow.

DETAILED DESCRIPTION OF THE INVENTION

As previously discussed, aberrant angiogenesis is associated with a number of disorders including tumor metastasis. Additionally, endothelial cells are associated with angiogenesis. In the present invention, fragments, conformations, biological equivalents, or derivatives of AT3 may exhibit anti-angiogenic and anti-tumor activity. For example, the R and L forms of AT3 are endothelial cell specific. Thus, this invention provides for methods of reducing or inhibiting angiogenesis, tumor growth and endothelial proliferations using fragments, conformations, biological equivalents, or derivatives of AT3. The invention also provides for methods of identifying inhibitors of tumor growth, endothelial cell proliferation, and/or angiogenesis. The invention also provides for pharmaceutical compositions comprising a fragment, conformation, biological equivalent, or derivative of AT3. The elements of the invention will now be discussed.

AT3 can be derived from any organism which produces the protein in nature. In a particular embodiment the organism is bovine or human. The amino acid sequence of bovine AT3 is available under GenBank Accession No. 1168462, and the amino acid sequence of human AT3 is available under GenBank Accession No. 113936 (SEQ ID NO:1).

AT3 can be isolated from body fluids such as serum, ascites and urine. AT3 can also be synthesized chemically or biologically, such as by cell culture or recombinant technology, or produced transgenically. Similarly, the particular portions and conformations of AT3, which are the subject of this invention, can be isolated from natural sources, produced transgenically, or can be chemically or biologically synthesized, such as by guanidine treatment or in vitro cleavage of AT3. Recombinant techniques known in the art include, but are not limited to, gene amplification from DNA using polymerase chain reaction (PCR), gene amplification from RNA using reverse transcriptase PCR and NASBA (nucleic acid sequence based amplifications).

The particular portions and conformations of AT3 or its biological equivalents, which are the subject of this invention, may also be produced by the use of an enzyme (e.g. elastase) in vivo. For example, an enzyme may be used in vivo, with or without plasma or native AT3 to serve as an additional substrate, to produce a fragment, conformation, biological equivalent, or derivative of AT3 that inhibits endothelial cell proliferation, angiogenesis and/or tumor growth.

AT3 is a member of the serpin family of proteins and functions as an inhibitor of thrombin and other enzymes involved in the clotting cascade. Serpins are a family of proteins that function as serine protease inhibitors. As used herein, the active native intact form of AT3 is designated the S (stressed) form (S-AT3). S-AT3 (FIG. 1A) is referred to as the "stressed" form of AT3 due to the fact that it is a metastable conformation with the reactive center loop (RCL) extended. This is the active form of AT3 in terms of inhibition of thrombin and other serine proteases.

Figure 2:
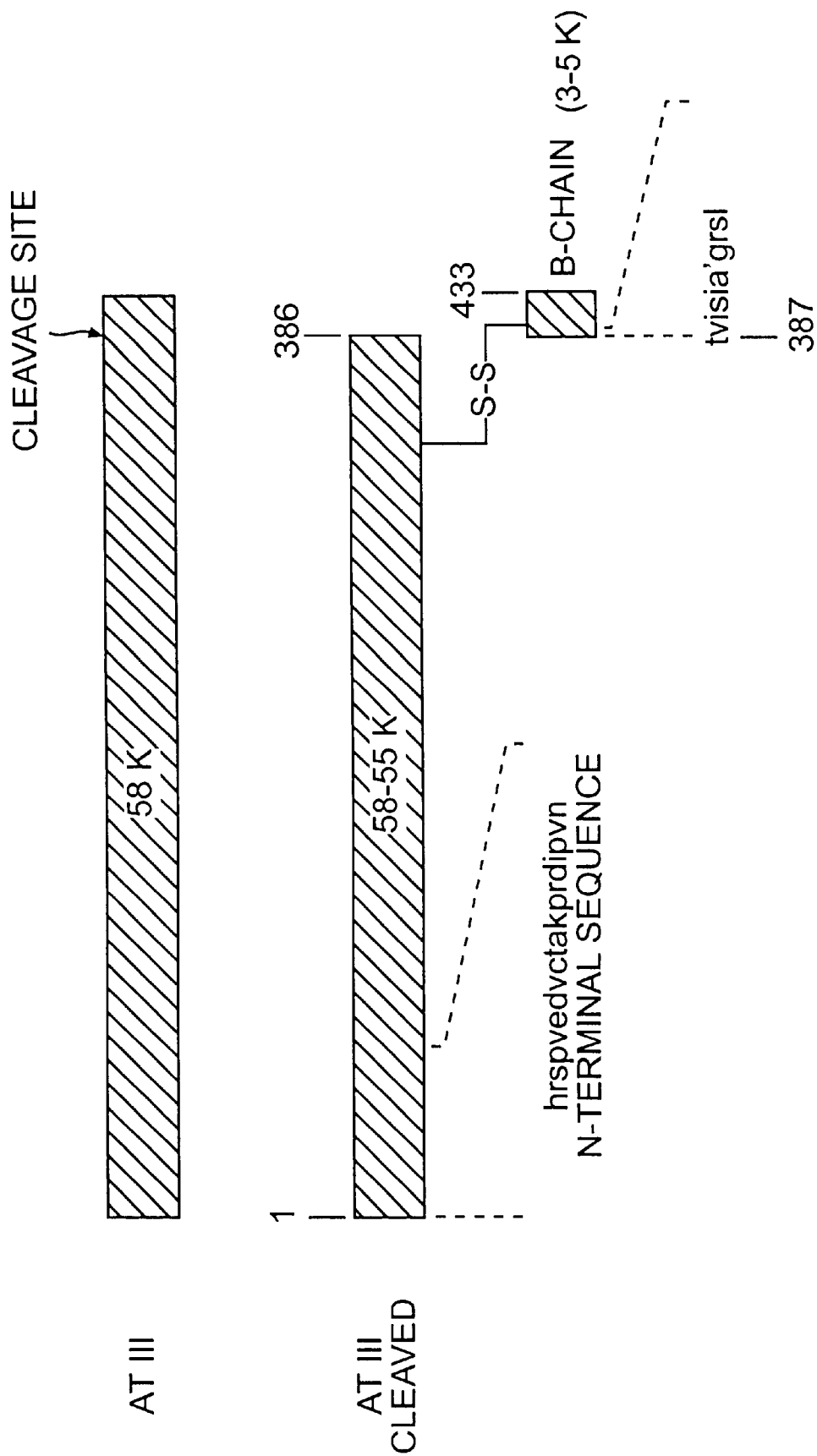

S-AT3 can be cleaved to the relaxed (R)-conformation (R-AT3) by a variety of enzymes, including thrombin. R-AT3 (FIG. 1A) is referred to as the "relaxed" form due i to the fact that the RCL has been cleaved by one of several proteases, including thrombin and elastase. This results in the insertion of the N-terminal half of the loop as a sixth strand into the A-beta sheet of AT3 to give a much more stable conformation than for the S-AT3 form. This form is no longer active as an inhibitor of serine proteases. For example, thrombin binds to a reactive C-terminal loop of AT3 and the resultant complex slowly dissociates releasing thrombin and cleaving off the C-terminal loop of inactive AT3, resulting in R-AT3. In particular, R-AT3 can be generated by enzyme cleavage of S-AT3 between $Arg_{393}$ and $Ser_{394}$ (human AT3 numbering). The amino acid sequence of human AT3 and the pancreatic elastase cleavage site of the c-terminal reactive loop are shown in FIG. 1B. (For bovine R-AT3, the cleavage site is between $Ser_{386}$ and $Thre_{387}$ as shown in FIG. 2.) The cleaved AT3 consists of disulfide-bonded A- and B-chains and is unable to bind thrombin. The cleavage occurs spontaneously even at cold temperatures resulting in the R form of AT3. Enzymes suitable for this cleavage include, but are not limited to, pancreatic elastase and thrombin. R-AT3 is unable to inhibit thrombin and has a conformation that is quite different from that of S-AT3. The role of R-AT3 had only been known to facilitate hepatic clearance of the molecule.

L-AT3 (FIG. 1A) is a group of forms of AT3 that includes the both the latent form and the locked form. These forms are structurally similar to the R-AT3 form in that all or part of the N-terminal half of the RCL has been inserted as a sixth strand into the A-beta sheet of AT3, resulting in a more stable conformation that is no longer active as a serine protease inhibitor. In the case of the "L-forms" however, there is no cleavage of the loop. The latent conformation is a monomeric L-form, while the locked conformation also includes dimers and oligomers, which are formed by insertion of the RCL from one AT3 molecule into the A-beta sheet of another.

Surprisingly, it has been determined that certain conformations of AT3 reduce angiogenesis, endothelial cell proliferation, and tumor growth. (As used herein, endothelial cell proliferation also includes endothelial cell migration and tube formation.) For example, R-AT3 has potent anti-angiogenic and anti-tumor activity which is not found in S-AT3. Additionally, the stable locked and latent forms (L-AT3) of S-AT3, which are substantially similar in conformation to R-AT3, also reduce or inhibit angiogenesis and tumor growth in vivo and are endothelial cell specific in vitro. The invention relates to methods of inhibiting endothelial cell proliferation, angiogenesis and/or tumor growth in a mammal comprising delivering or administering to the mammal a composition comprising a fragment, conformation, biological equivalent, or derivative of AT3, including but not limited to L-AT3 and R-AT3, and an optional physiologically acceptable vehicle. As described herein, fragments conformations, derivatives and biological equivalents of AT3 include, but are not limited to: other serpins and their conformational variations; fragments; conformations; aggregate forms; and fusion proteins; which are active as inhibitors of angiogenesis, endothelial cell proliferation and/or tumor growth. The invention also relates to a method of treating a disorder mediated by angiogenesis or endothelial cell proliferation comprising administering a composition comprising a fragment, conformation, derivative or biological equivalent of AT3, including but not limited to L-AT3 and R-AT3, and an optional physiologically acceptable vehicle to a mammal. The invention further relates to a method of treating cancer comprising administering a composition comprising an effective amount of a fragment, conformation, derivative or biological equivalent of AT3, including but not limited to L-AT3 and R-AT3, and an optional physiologically acceptable vehicle to a mammal.

The invention also relates to a method of enhancing angiogenesis or endothelial cell proliferation comprising administering a composition comprising an effective amount of an antagonist of AT3, e.g., an antagonist of S-AT3, an antagonist of R-AT3 or an antagonist of L-AT3 to a mammal. For example, this method can be useful in the treatment of abnormal ovulation, menstruation and placentation, and vasculogenesis, such as in tissue repair, wound healing and tissue grafting.

The fragments, conformations, derivatives, and biological equivalents of AT3 having anti-angiogenic properties, that inhibit the proliferation of endothelial cells, and/or have anti-tumor activity are described herein. These AT3 fragments, conformations, derivatives and biological equivalents are collectively termed herein "anti-angiogenic AT3 products," "anti-proliferative AT3 products," aaAT, or aaAT3.

In addition to the sequences of AT3 described above, useful nucleic acid molecules may comprise a nucleotide sequence which is greater than about 80 percent, preferably greater than about 85 percent, more preferably greater than about 90 percent, and even more preferably greater than about 95 percent, identical to the nucleotide sequences of S-AT3, R-AT3 and L-AT3 deposited in GenBank. The substantially identical sequence should, however, retain at least one of the activities of inhibition of endothelial cell proliferation, inhibition of angiogenesis or inhibition of tumor growth (i.e., a biological equivalent).

To determine the percent identity of two nucleotide sequences, the sequences are aligned for optimal comparison purposes (e.g., gaps can be introduced in the sequence of a first nucleotide sequence). The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences (i.e., % identity=# of identical positions/total # of positions× 100).

The determination of percent identity between two sequences can be accomplished using a mathematical algorithm. A preferred, non-limiting example of a mathematical algorithm utilized for the comparison of two sequences is the algorithm of Karlin et al., *Proc. Mad. Acad. Sci. USA*, 90:5873–5877 (1993). Such an algorithm is incorporated into the NBLAST program which can be used to identify sequences having the desired identity to nucleotide sequences of the invention. To obtain gapped alignments for comparison purposes, Gapped BLAST can be utilized as described in Altschul et al., *Nucleic Acids Res*, 25:3389–3402 (1997). When utilizing BLAST and Gapped BLAST programs, the default parameters of the respective programs (e.g., NBLAST) can be used. In one embodiment, parameters for sequence comparison can be set at W=12. Parameters can also be varied (e.g., W=5 or W=20). The value "W" determines how many continuous nucleotides must be identical for the program to identify two sequences as containing regions of identity.

As appropriate, nucleic acid molecules of the present invention can be RNA, for example, mRNA, or DNA, such as cDNA and genomic DNA. DNA molecules can be double-stranded or single-stranded; single stranded RNA or DNA can be either the coding, or sense, strand or the non-coding, or antisense, strand. Preferably, the nucleic acid molecule comprises at least about 10 nucleotides, more preferably at least about 50 nucleotides, and even more preferably at least about 200 nucleotides. The nucleic acid molecule can include all or a portion of the coding sequence of a gene and can further comprise additional non-coding sequences such as introns and non-coding 3' and 5' sequences (including regulatory sequences, for example). Additionally, the nucleic acid molecule can be fused to a marker sequence, for example, a sequence which encodes a polypeptide to assist in isolation or purification of the polypeptide. Such sequences include, but are not limited to, those which encode a glutathione-S-transferase (GST) fusion protein and those which encode a hernaglutin A (HA) polypeptide marker from influenza.

As used herein, an "isolated" gene or nucleic acid molecule is intended to mean a gene or nucleic acid molecule which is not flanked by nucleic acid molecules which normally (in nature) flank the gene or nucleic acid molecule (such as in genomic sequences) and/or has been completely or partially purified from other transcribed sequences (as in a cDNA or RNA library). For example, an isolated nucleic acid of the invention may be substantially isolated with respect to the complex cellular milieu in which it naturally occurs. In some instances, the isolated material will form part of a composition (for example, a crude extract containing other substances), buffer system or, reagent mix. In other circumstance, the material may be purified to essential homogeneity, for example as determined by PAGE or column chromatography such as HPLC. Preferably, an isolated nucleic acid comprises at least about 50, 80 or 90 percent (on a molar basis) of all macromolecular species present. Thus, an isolated gene or nucleic acid molecule can include a gene or nucleic acid molecule which is synthesized chemically or by recombinant means. Recombinant DNA contained in a vector is included in the definition of "isolated" as used herein. Also, isolated nucleic acid molecules include recombinant DNA molecules in heterologous host cells, as well as partially or substantially purified DNA molecules in solution. In vivo and in vitro RNA transcripts of the DNA molecules of the present invention are also encompassed by "isolated" nucleic acid molecules. Such isolated nucleic acid molecules are useful in the manufacture of the encoded protein, as probes for isolating homologous sequences (e.g., from other mammalian species), for gene mapping (e.g., by in situ hybridization with chromosomes), or for detecting expression of the gene in tissue (e.g., human tissue) such as by Northern blot analysis.

Thus, DNA molecules which comprise a sequence which is different from the naturally-occurring nucleic acid molecule, but which, due to the degeneracy of the genetic code, encode a substantially similar protein or polypeptide are useful in this invention. The invention also encompasses variations of the nucleic acid molecules of the invention, such as those encoding portions, analogues or derivatives of the encoded protein or polypeptide. Such variations can be naturally-occurring, such as in the case of allelic variation, or non-naturally-occurring, such as those induced by various mutagens and mutagenic processes. Intended variations include, but are not limited to, addition, deletion and substitution of one or more nucleotides which can result in conservative or non-conservative amino acid changes, including additions and deletions. Preferably, the nucleotide variations are silent; that is, they do not alter the characteristics or activity of the encoded protein or polypeptide (i.e., a biological equivalent). As used herein, activities of the encoded protein or polypeptide include, but are not limited to, inhibition of angiogenesis, inhibition of endothelial cell proliferation and inhibition of tumor growth. The invention also encompasses sequences that are not identical to AT3.

The invention also pertains to nucleic acid molecules which hybridize under high stringency hybridization conditions (e.g., for selective hybridization) to a nucleotide sequence described herein. Hybridization probes are oligonucleotides which bind in a base-specific manner to a complementary strand of nucleic acid. Such probes include polypeptide nucleic acids, as described in Nielsen et al., Science 254, 14971500 (1991). Such nucleic acid molecules can be detected and/or isolated by specific hybridization (e.g., under high stringency conditions). "Stringency conditions" for hybridization is a term of art which refers to the incubation and wash conditions, e.g., conditions of temperature and buffer concentration, which permit hybridization of a particular nucleic acid to a second nucleic acid; the first nucleic acid may be perfectly (i.e., 100%) complementary to the second, or the first and second may share some degree of complementarity which is less than perfect (e.g., 60%, 75%, 85%, 95%). For example, certain high stringency conditions can be used which distinguish perfectly complementary nucleic acids from those of less complementarity. "High stringency conditions", "moderate stringency conditions" and "low stringency conditions" for nucleic acid hybridizations are explained on pages 2.10.1–2.10.16 and pages 6.3.1–6 in *Current Protocols in Molecular Biology* (Ausubel, F. M. et al., "*Current Protocols in Molecular Biology*", John Wiley & Sons, (1998)) the teachings of which are hereby incorporated by reference. Equivalent conditions can be determined by varying one or more of the parameters given as an example, as known in the art, while maintaining a similar degree of identity or similarity between the target nucleic acid molecule and the primer or probe used. Hybridizable nucleic acid molecules are useful as probes and primers, e.g., for diagnostic applications.

In addition to substantially full-length polypeptides encoded by nucleic acid molecules described herein, the present invention includes biologically active fragments of the S-AT3, R-AT3 and L-AT3 biological equivalents, or analogs thereof, including organic molecules which simulate the interactions of S-AT3, R-AT3 or L-AT3. Biologically active fragments include any portion of the full-length polypeptide which confers a biological function on the variant gene product, including ligand binding and antibody binding, and particularly including inhibition of endothelial cell proliferation, angiogenesis or tumor growth.

Also of use in the invention are fragments or portions of the isolated nucleic acid molecules described above. The term "fragment" is intended to encompass a portion of a nucleic acid molecule described herein which is from at least about 7 contiguous nucleotides to at least about 25 contiguous nucleotides or longer in length. Such fragments are useful as probes, e.g., for diagnostic methods, and also as primers. The nucleotide sequences may also be an isolated portion of any of the nucleotide sequences of S-AT3, R-AT3 and L-AT3, which portion is sufficient in length to distinctly characterize the sequence. Particularly preferred primers and probes selectively hybridize to the nucleotide sequences of S-AT3, R-AT3 and L-AT3. For example, fragments which encode antigenic proteins or polypeptides described herein are useful.

Also within the practice of the invention are anti-angiogenic AT3 products and anti-proliferative AT3 products that are intended to encompass any fragments or conformations (e.g., the L conformation) of AT3 which have anti-angiogenic and/or anti-proliferative activity, respectively. Anti-angiogenic activity and anti-proliferative activity can be assessed according to methods described herein or according to other methods known in the art or may be any fragments or biological equivalents that mimic the active site.

The biological equivalents of AT3, may include, but are not limited to, fragments of S-AT3, R-AT3, and L-AT3 that comprise the active site; synthetic compounds that mimic the active site; conformational variations of other serpins; other conformations of AT3, aggregate forms and fusion proteins that exhibit anti-angiogenic and anti-proliferative properties. Conformational variations of other serpins that may be useful in the practice of the invention include but are not limited to plasminogen activator inhibitor-1 (PAI-1), $\alpha_2$ antiplasmin, $\alpha 1$ proteinase inhibitor, heparin cofactor II, C1 inhibitor, $\alpha 1$ antichymotrypsin, protease nexin 1, and pigment epithelial derived factor.

This invention also pertains to an isolated protein or polypeptide encoded by the nucleic acid molecules of the invention. The encoded proteins or polypeptides of the invention can be partially or substantially purified (e.g., purified to homogeneity), and/or are substantially free of other proteins. According to the invention, the amino acid sequence of the polypeptide can be that of the naturally-occurring protein or can comprise alterations therein. Such alterations include conservative or non-conservative amino acid substitutions, additions and deletions of one or more amino acids; however, such alterations should preserve at least one activity of the encoded protein or polypeptide, i.e., the altered or mutant protein should be a biological equivalent of the naturally-occurring protein. The mutation(s) should preferably preserve the endothelial cell proliferative inhibition, angiogenesis inhibition or tumor growth inhibition activities of the native protein or polypeptide. The presence or absence of biological activity or activities can be determined by various functional assays as described herein. For example, glycosylation variants of AT3, along with β-AT3 (Olson et al., *Archives of Biochemistry and Biophysics* 341(2): 212–221 (1997)) are within the scope of the biological equivalents of AT3. The β-AT3 form may also be useful as described herein.

Moreover, amino acids which are essential for the function of the encoded protein or polypeptide can be identified by methods known in the art. Particularly useful methods include identification of conserved amino acids in the family or subfamily, site-directed mutagenesis and alanine-scanning mutagenesis (for example, Cunningham and Wells, *Science* 244:1081–1085 (1989)), crystallization and nuclear magnetic resonance. The altered polypeptides produced by these methods can be tested for particular biologic activities, including immunogenicity and antigenicity.

Specifically, appropriate amino acid alterations can be made on the basis of several criteria, including hydrophobicity, basic or acidic character, charge, polarity, size, the presence or absence of a functional group (e.g., —SH or a glycosylation site), and aromatic character. Assignment of various amino acids to similar groups based on the properties above will be readily apparent to the skilled artisan; further appropriate amino acid changes can also be found in Bowie et al., *Science* 247:1306–1310(1990).

For example, conservative amino acid replacements can be those that take place within a family of amino acids that are related in their side chains. Genetically encoded amino acids are generally divided into four families: (1) acidic=aspartate, glutamate; (2) basic=lysine, arginine, histidine; (3) nonpolar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan and tyrosine are sometimes classified jointly as aromatic amino acids. For example, it is reasonable to expect that an isolated replacement of a leucine with an isoleucine or valine, an aspartate with a glutamate, a threonine with a serine or a similar conservative replacement of an amino acid with a structurally related amino acid will not have a major effect on activity or functionality.

The polypeptides of the present invention can be used to raise antibodies or to elicit an immune response. The polypeptides can also be used as a reagent, e.g., a labeled reagent, in assays to quantitatively determine levels of the protein or a molecule to which it binds (e.g., a receptor or a ligand) in biological fluids. The polypeptides can also be used as markers for tissues in which the corresponding protein is preferentially expressed, either constitutively, during tissue differentiation, or in a diseased state. The polypeptides can be used to isolate a corresponding binding partner, e.g., receptor or ligand, such as, for example, in an interaction trap assay, and to screen for peptide or small molecule antagonists or agonists.

The present invention also relates to antibodies which bind a polypeptide or protein of the invention. For instance, polyclonal and monoclonal antibodies, including non-human and human antibodies, humanized antibodies, chimeric antibodies and antigen-binding fragments thereof (*Current Protocols in Immunology*, John Wiley & Sons, N.Y. (1994); EP Application 173,494 (Morrison); International Patent Application WO86/01533 (Neuberger); and U.S. Pat. No. 5,225,539 (Winters)) which bind to the described S-AT3, R-AT3 or L-AT3 proteins or polypeptides are within the scope of the invention. A mammal, such as a mouse, rat, hamster or rabbit, can be immunized with an immunogenic form of the protein (e.g., the fall length protein or a polypeptide comprising an antigenic fragment of the protein which is capable of eliciting an antibody response). Techniques for conferring immunogenicity on a protein or polypeptide include conjugation to carriers or other techniques well known in the art. The protein or polypeptide can be administered in the presence of an adjuvant. The progress of immunization can be monitored by detection of antibody titers in plasma or serum. Standard ELISA or other immunoassays can be used with the immunogen as antigen to assess the levels of antibody.

As described herein, AT3 and/or a fragment, conformation, biological equivalent, or derivative can be made or isolated by numerous methods known in the art, including, but not limited to, purification, transgenic and recombinant methods.

The invention provides expression vectors containing a nucleic acid sequence described herein, operably linked to at least one regulatory sequence. Many such vectors are commercially available, and other suitable vectors can be readily prepared by the skilled artisan. "Operably linked" or "operatively linked" is intended to mean that the nucleic acid molecule is linked to a regulatory sequence in a manner which allows expression of the nucleic acid sequence. Regulatory sequences are art recognized and are selected to produce the encoded polypeptide or protein. Accordingly, the term "regulatory sequence" includes promoters, enhancers, and other expression control elements which are described in Goeddel, *Gene Expression Technology: Methods in Enzymology* 185, Academic Press, San Diego, Calif. (1990). For example, the native regulatory sequences or regulatory sequences native to the transformed host cell can be employed. It should be understood that the design of the expression vector may depend on such factors as the choice of the host cell to be transformed and/or the type of protein desired to be expressed. For instance, the polypeptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression*, ed. M. Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17). Typically, expression constructs will contain one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells transfected by the described vectors are also provided by this invention. For instance, cells which can be transfected with the vectors of the present invention include, but are not limited to, bacterial cells such as *E. coli* (e.g., *E. coli* K12 strains), Streptomyces, Pseudomonas, *Serratia marcescens* and *Salmonella typhimurium*, insect cells (baculovirus), including Drosophila, fungal cells, such as yeast cells, plant cells and mammalian cells, such as thymocytes, Chinese hamster ovary cells (CHO), and COS cells.

In one embodiment, at least one fragment, conformation, biological equivalent, or derivative of AT3 that is useful in the practice of the invention is produced in vivo or ex vivo via gene therapy. For example, gene therapy may be used to produce AT3 or a biological equivalent. An enzyme that effectuates a conformational change in AT3 or a biological equivalent to an anti-angiogenic product is then delivered to the AT3 or the biological equivalent. Gene therapy may be used to produce an enzyme that effectuates a conformational change in AT3 or a biological equivalent to an anti-angiogenic product, or both an enzyme and AT3 or a biological equivalent. By using tissue specific expression an anti-angiogenic product may be produced in vivo at a desired site.

Thus, a nucleic acid molecule described herein can be used to produce a recombinant form of the protein via microbial or eukaryotic cellular processes. Ligating the polynucleic acid molecule into a gene construct, such as an expression vector, and transforming or transfecting into hosts, either eukaryotic (yeast, avian, insect, plant or mammalian) or prokaryotic (bacterial cells), are standard procedures used in producing other well known proteins. Similar procedures, or modifications thereof, can be employed to prepare recombinant proteins according to the present invention by microbial means or tissue-culture technology. Accordingly, the invention pertains to the production of encoded proteins or polypeptides by recombinant technology.

The proteins and polypeptides of the present invention can be isolated or purified (e.g., to homogeneity) from recombinant cell culture by a variety of processes. These include, but are not limited to, anion or cation exchange chromatography, ethanol precipitation, affinity chromatography and high performance liquid chromatography (HPLC). The particular method used will depend upon the properties of the polypeptide and the selection of the host cell; appropriate methods will be readily apparent to those skilled in the art.

Following immunization, anti-peptide antisera can be obtained, and if desired, polyclonal antibodies can be isolated from the serum. Monoclonal antibodies can also be produced by standard techniques which are well known in the art (Kohler and Milstein, *Nature* 256:495–497 (1975); Kozbar et al., *Immunology Today* 4:72 (1983); and Cole et al., *Monoclonal Antibodies and Cancer Therapy*, Alan R. Liss, Inc., pp. 7796 (1985)). The term "antibody" as used herein is intended to include fragments thereof, such as Fab and F(ab)2. Antibodies described herein can be used to inhibit the activity of the polypeptides and proteins described herein, particularly in vitro and in cell extracts, using methods known in the art. Additionally, such antibodies, in conjunction with a label, such as a radioactive label, can be used to assay for the presence of the expressed protein in a cell from, e.g., a tissue sample, and can be used in an immunoabsorption process, such as an ELISA, to isolate the protein or polypeptide. Tissue samples which can be assayed include human tissues, e.g., differentiated and non-differentiated cells, such as tumor cells. These antibodies are useful in diagnostic assays, or as an active ingredient in a pharmaceutical composition. For example, passive antibody therapy using antibodies which specifically bind S-AT3, R-AT3 or L-AT3 can be used to modulate (inhibit or enhance) endothelial cell proliferative- or angiogenic-dependent processes such as reproduction, wound healing and tissue repair.

The present invention also encompasses the detection of conformations including but not limited to S-AT3, R-AT3, and L-AT3, fragments, derivatives, conformational variations of other serpins, and biological equivalents of AT3 in bodily fluids to determine the diagnosis or prognosis of endothelial cell proliferation related or angiogenesis-related disorders. As used herein, angiogenesis-related disorders include, but are not limited to, cancers, solid tumors, blood born tumors such as leukemias, tumor metastasis, benign tumors such as hemangiomas, acoustic neuromas, neurofibromas, trachomas and pyogenic granulomas, rheumatoid arthritis, psoriasis, ocular anglogenic diseases such as diabetic retinopathy, retinopathy of prematurity, macular degeneration, corneal graft rejection, neovascular glaucoma, retrolental fibroplasia and rubeosis, Osler-Webber Syndrome, myocardial angiogenesis, plaque neovascularization, telangiectasia, hemophiliac joints, angiofibroma and wound granulation. As used herein, endothelial cell proliferation-related disorders include, but are not limited to, intestinal adhesions, atherosclerosis, scleroderma and hypertrophic scars. Compounds described herein can also be used as birth control agents by preventing the neovascularization required for embryo implantation.

The invention also relates to a kit for detecting the presence of fragments, conformations, derivatives, and biological equivalents of AT3, including S-AT3, R-AT3 or L-AT3 in bodily fluids. Typically, the kit will comprise primary reagents (e.g., antibodies) capable of detecting the presence of fragments, conformations, derivatives, and biological equivalents in a sample. The kit may also comprise adjunct reagents suitable for detecting binding of the primary reagent to the target.

The present invention also pertains to pharmaceutical compositions comprising fragments, conformations, derivatives, and biological equivalents of AT3 including polypeptides and other compounds described herein. For instance, a polypeptide or protein, or prodrug thereof, of the present invention can be formulated with a physiologically acceptable medium to prepare a pharmaceutical composition. In one embodiment, an anti-angiogenic pharmaceutical composition comprises a purified form of AT3 that reduces angiogenesis. In a preferred embodiment the purified form of AT3 is the L form or R form of AT3 or a fragment or sequence which includes the active site or region of the L form or R form of AT3. The particular physiological medium may include, but is not limited to, water, buffered saline, polyols (e.g., glycerol, propylene glycol, liquid polyethylene glycol) and dextrose solutions. The optimum concentration of the active ingredient(s) in the chosen medium can be determined empirically, according to well known procedures, and will depend on the ultimate pharmaceutical formulation desired. Formulation of an agent to be administered will vary according to the route of administration selected (e.g., solution, emulsion, capsule). An appropriate composition comprising the agent to be administered can be prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils, for instance. Intravenous vehicles can include various additives, preservatives, or fluid, nutrient or electrolyte replenishers and the like (See, generally, *Remington's Pharmaceutical Sciences*, 17$^{th}$ Edition, Mack Publishing Co., PA, 1985). For inhalation, the agent can be solubilized and loaded into a suitable dispenser for administration (e.g., an atomizer, nebulizer or pressurized aerosol dispenser).

The pharmaceutical compositions of the present invention may also comprise a composition that effectuates a conformational change in a serpin or produces a fragment, conformation, derivative, and biological equivalent of AT3 in vivo, for example, by the delivery of an enzyme.

Methods of introduction at the site of treatment include, but are not limited to, intradermal, intramuscular, intra peritoneal, intravenous, rectal, vaginal, intra ocular, topical, subcutaneous, oral and intra nasal. Other suitable methods of introduction can also include gene therapy, rechargeable or biodegradable devices, viral vectors, naked DNA, lipids and slow release polymeric devices. The pharmaceutical compositions of this invention can also be administered as part of a combinatorial therapy with other agents. Nucleic acid sequences of the invention can be used in gene therapy and introduced either in vivo or ex vivo into cells for expression in a mammalian subject. Cells can also be cultured ex vivo in the presence of proteins of the present invention in order to produce a desired effect on such cells. Treated cells can then be introduced in vivo for therapeutic purposes.

The invention can be used to treat a variety of animals. Suitable animals as used herein include mammals, including, but not limited to, primates (e.g., humans), dogs, cats, cows, horses, pigs, sheep, goats and rodents (e.g., rats, mice and hamsters). Appropriate dosages (e.g., those containing an "effective amount") of a fragment, conformation, derivative or biological equivalent of AT3 will depend upon the physical characteristics of the animal to be treated and on the disorder and (progression thereof) to be treated. One of ordinary skill in the art would readily be able to determine what would be an effective amount. The agent can be administered alone or in combination with other agents or treatment regimes, including chemotherapy and radiation. The agent can be administered in multiple or single administrations provided sequentially or simultaneously.

It is also a subject of this invention to provide a new method for identifying an inhibitor of tumor growth or an agent that reduces tumor growth. Prior methods typically required that two separate tumor inoculations or implants be carried out, the second being performed substantially later than the first. The reason for this approach was that it was thought that if the second tumor implant occurred at the same time, or shortly after, the primary tumor was implanted, the primary tumor would not be able to suppress the secondary tumor, because by the time the primary tumor reached sufficient size to release the inhibitors continuously into the circulation, angiogenesis in the secondary tumor would already be well underway. Similarly, it was also believed that if two tumors were implanted simultaneously (e.g., in opposite flanks), the inhibitors would have an equivalent inhibiting effect on each other.

Work described herein has shown that tumor implants or inoculations can in fact be carried out substantially simultaneously in an animal in an effort to identify inhibitors of tumor growth. As used herein, "substantially simultaneously" means that the tumor implants or inoculations occur at the same time or closely in sequence; there is no requirement that one tumor be implanted or inoculated first and allowed to grow to a particular size. The method of this invention therefore provides a substantial reduction in the time necessary to carry out the screening, as it is not necessary to wait for the first tumor to grow before implanting the second.

According to the method of the invention, an animal (e.g., a mammal such as a mouse, rat, guinea pig or primate) is inoculated with an appropriate inoculum of tumor cells in each of two suitable inoculation sites substantially simultaneously. An appropriate inoculum of tumor cells is an amount of tumor cells sufficient to cause formation of a tumor, and is intended to include implantation of preformed tumors such as micrometastasis. The tumor cells can be derived from any tumors; for example, the tumors can include, but are not limited to, small cell lung cancers and hepatocellular carcinomas. Appropriate inoculation sites include, but are not limited to, the subcutaneous space, the cornea, the lung, the breast, the prostate, the testes and the brain. In a preferred embodiment, the inoculation sites are the flanks of the animal.

The tumors are allowed to grow in the animal, and inhibition of growth of one tumor, known as the subordinate tumor, with concomitant growth of the other tumor, known as the dominant tumor, is identified. Tumor size can be measured using methods known in the art, such as by measuring the diameter of the tumor using calipers. Using methods described herein and known in the art, such as selective in vivo passaging, dominant tumors can be selected which substantially completely inhibit the growth of the subordinate tumor. As used herein, "substantially completely" is intended to include greater than about 80% inhibition of growth of the subordinate tumor. In a preferred embodiment, the inhibition is greater than about 90%, and in a particularly preferred embodiment, the inhibition is near 100%. However, dominant tumors which inhibit the growth of the subordinate tumor to any degree are useful.

Once a suitable dominant tumor is identified, the component(s) which inhibits tumor growth can be purified from the tumor. For example, the tumor can be grown in vitro and the component can be purified from conditioned media from the tumor cells using methods described herein or other methods known in the art. With respect to protein or polypeptide identification, bands identified by gel analysis can be isolated and purified by HPLC, and the resulting purified protein can be sequenced. Alternatively, the purified protein can be enzymatically digested by methods known in the art to produce polypeptide fragments which can be sequenced. The sequencing can be performed, for example, by the methods of Wilm et al. *Nature* 379(6564):466–469 (1996). The protein may be isolated by conventional means of protein biochemistry and purification to obtain a substantially pure product, i.e., 80, 95 or 99% free of cell component contaminants, as described in Jacoby, *Methods in Enzymology* Volume 104, Academic Press, New York (1984); Scopes, *Protein Purification, Principles and Practice,* 2nd Edition, Springer-Verlag, New York (1987); and Deutscher (ed), *Guide to Protein Purification, Methods in Enzymology,* Vol. 182 (1990). If the protein is secreted, it can be isolated from the supernatant in which the host cell is grown. If not secreted, the protein can be isolated from a lysate of the host cells.

Potential inhibitors can be tested in endothelial cell proliferation assays and/or angiogenesis assays (e.g., a CAM assay) to identify inhibitors of endothelial cell proliferation and/or angiogenesis. For example, as described herein, bovine and human R-AT3 and L-AT3 were identified as inhibiting endothelial cell proliferation, angiogenesis and tumor growth.

Compounds identified by this method as inhibiting endothelial cell proliferation, angiogenesis and/or tumor growth can be used in both in vitro and in vivo methods to inhibit endothelial cell proliferation, angiogenesis and/or tumor growth as described herein for AT3. Furthermore, antagonists of identified compounds can be identified using art recognized methods. For example, an antagonist to be tested can be combined with the compound in an endothelial cell proliferation assay or angiogenesis assay, and the level of endothelial cell proliferation or angiogenesis can be assessed relative to the results in the absence of the putative antagonist. Antagonists can be nucleic acids, proteins or polypeptides, small biologically active molecules, or large cellular structures and can be used to enhance endothelial cell proliferation and/or angiogenesis, such as in wound healing. Use of compounds identified by this method for inhibition or enhancement of endothelial cell proliferation and/or angiogenesis and for inhibition of tumor growth, as well as novel compounds identified by this method, are within the scope of the invention.

The present invention will now be illustrated by the following Examples, which are not intended to be limiting in any way. The teachings of all references cited herein are incorporated herein by reference in their entirety.

EXAMPLES

Example 1

Purification of Bovine and Human Antithrombin III

Bovine calf serum was thawed and heat-inactivated (56C×20 minutes) and then stored at 4° C. for 14–21 days to allow for degradation of AT3 to the R form. Serum was diluted 3-fold with 10 mM Tris pH 7 and then applied to a CM Sepharose column (5×35 cm) coupled to a DEAE Sepharose column (5×35 cm) after equilibration with 10 mM Tris pH 7. Both columns were washed extensively with 10 mM Tris pH 7 and then uncoupled. The DEAE column was washed extensively with 50 mM NaCl in 10 m-M Tris and then coupled to a heparin Sepharose column (2.5×35 cm) which was equilibrated with 0.2 M NaCl 10 mM Tris pH 7. Bound protein from the DEAE column was eluted directly onto the heparin Sepharose column using 0.2 M NaCl 10 mM Tris pH 7 and the columns were uncoupled. The heparin Sepharose column was washed extensively with 0.5 M NaCl and then eluted with a continuous gradient of 0.6–2 M NaCl (550 ml total volume) followed by an additional 250 ml of 2 M NaCl. Fractions were collected and an aliquot of each was tested on capillary endothelial cells. Fractions that inhibited were pooled and concentrated using a NanoSpin 30K centrifugal concentrator.

Human plasma was centrifuged (10,000 rpm×30 minutes), filtered (0.45 μm), and diluted 3-fold with 10 mM Tris pH 7. The diluted plasma was then applied to a CM Sepharose column (5×35 cm) coupled to a DEAE Sepharose column (5×35 cm) after equilibration with 10 mM Tris pH 7. Both columns were washed extensively with 10 mM Tris pH 7 and then uncoupled. The DEAE column was washed extensively with 50 mm NaCl in 10 mM Tris and then coupled to a heparin Sepharose column (2.5×35 cm) which were equilibrated with 0.2 M NaCl 10 mM Tris pH 7. Bound protein from the DEAE column was eluted directly onto the heparin Sepharose column using 0.2 M NaCl 10 mM Tris pH 7 and the columns were uncoupled. The heparin Sepharose column was washed extensively with PBS followed by 0.5 M NaCl in 10 mM Tris pH 7 and then eluted with a continuous gradient of 0.6–2 M NaCl (550 ml total volume) followed by an additional 250 ml of 2 M NaCl. Purified intact native AT3 was cleaved with porcine pancreatic elastase to produce the R-conformation incubated at 4° C. in 0.9 M guanidine and then dialyzed against PBS to produce the L-conformation. Purity of the final samples were assessed by SDS-PAGE with silver staining. Protein concentration was determined using a Biorad assay.

Example 2

Production of R and L forms of Antithrombin III

Intact bovine and human AT3 were obtained from Sigma or Calbiochem, respectively, or from human plasma as described above. Human and bovine intact AT3 were incubated in 0.9 M guanidium chloride to produce the stable locked conformation (L form) of the molecule as described previously by Carrell et al. After 12 hours of incubation, guanidium chloride was removed by dialysis (30K membrane) in PBS and samples were concentrated. Alternatively, AT3 was cleaved with pancreatic elastase as described. In order to obtain complete cleavage, the method was modified and AT3 was incubated with elastase at a 1:5 molar ratio for 12 hours at 37° C. The reaction was quenched by applying the mixture to a heparin Sepharose column at 4° C. The cleaved AT3 was purified to homogeneity using heparin Sepharose and then concentrated using a Nanospin 30K centrifugal concentrator.

Example 3

Inhibitory Activity on Endothelial Proliferation

To determine if the inhibitory activity on endothelial cell proliferation of AT3 was specific, AT3 from bovine and human sources was screened on a panel of non-endothelial cell lines in vitro, as specificity in vitro may predict for lack of toxicity in vivo. Of all the cell types screened, only capillary endothelial cells were significantly inhibited even at log fold higher doses. The same specificity was seen for the L- and R forms of human and bovine AT3. The intact native (S-AT3) molecule had no significant effect on non-endothelial cells and only marginally inhibited capillary endothelial cells at doses in excess of 10 ug/ml.

Figure 3:
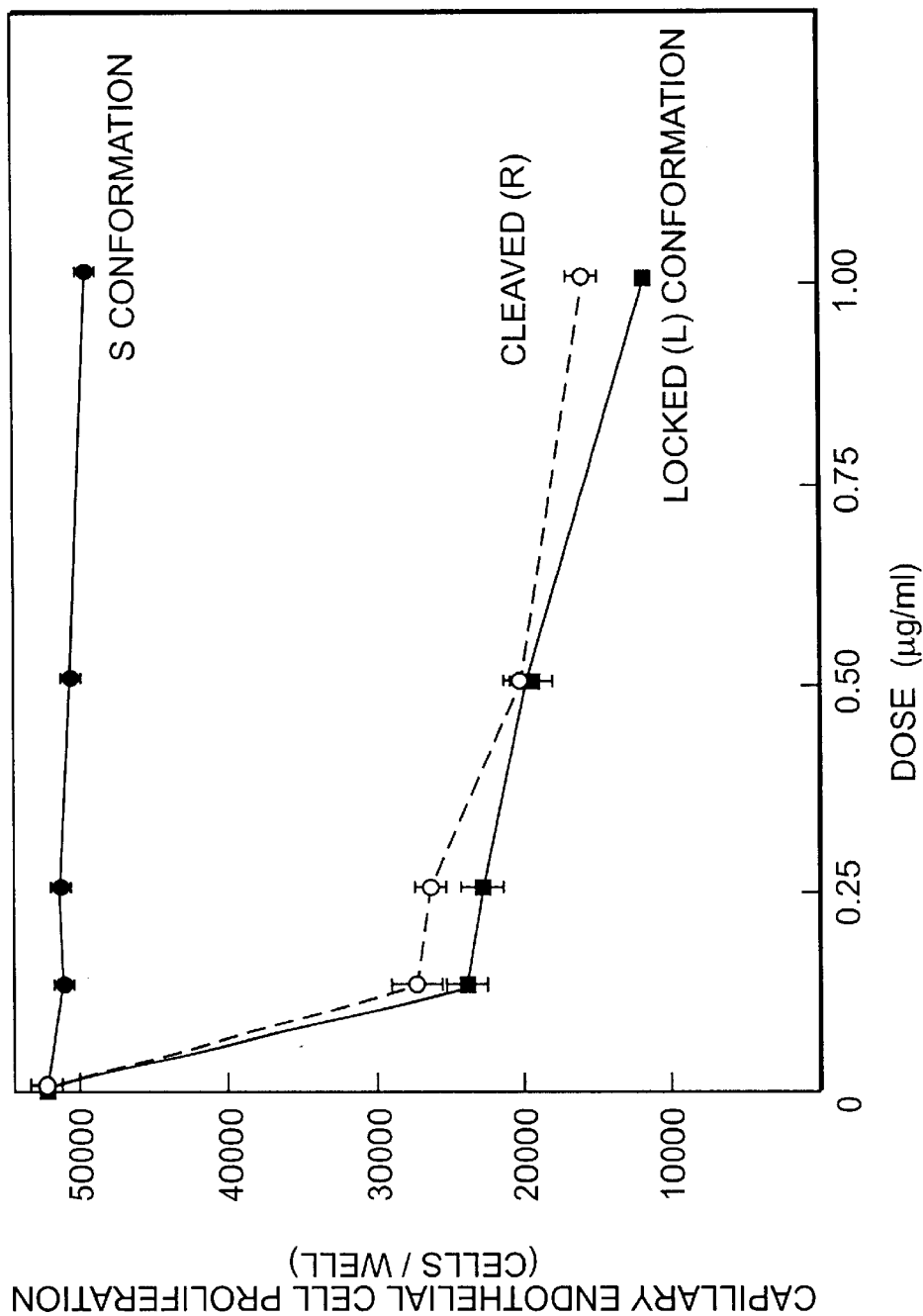
Figure 4:
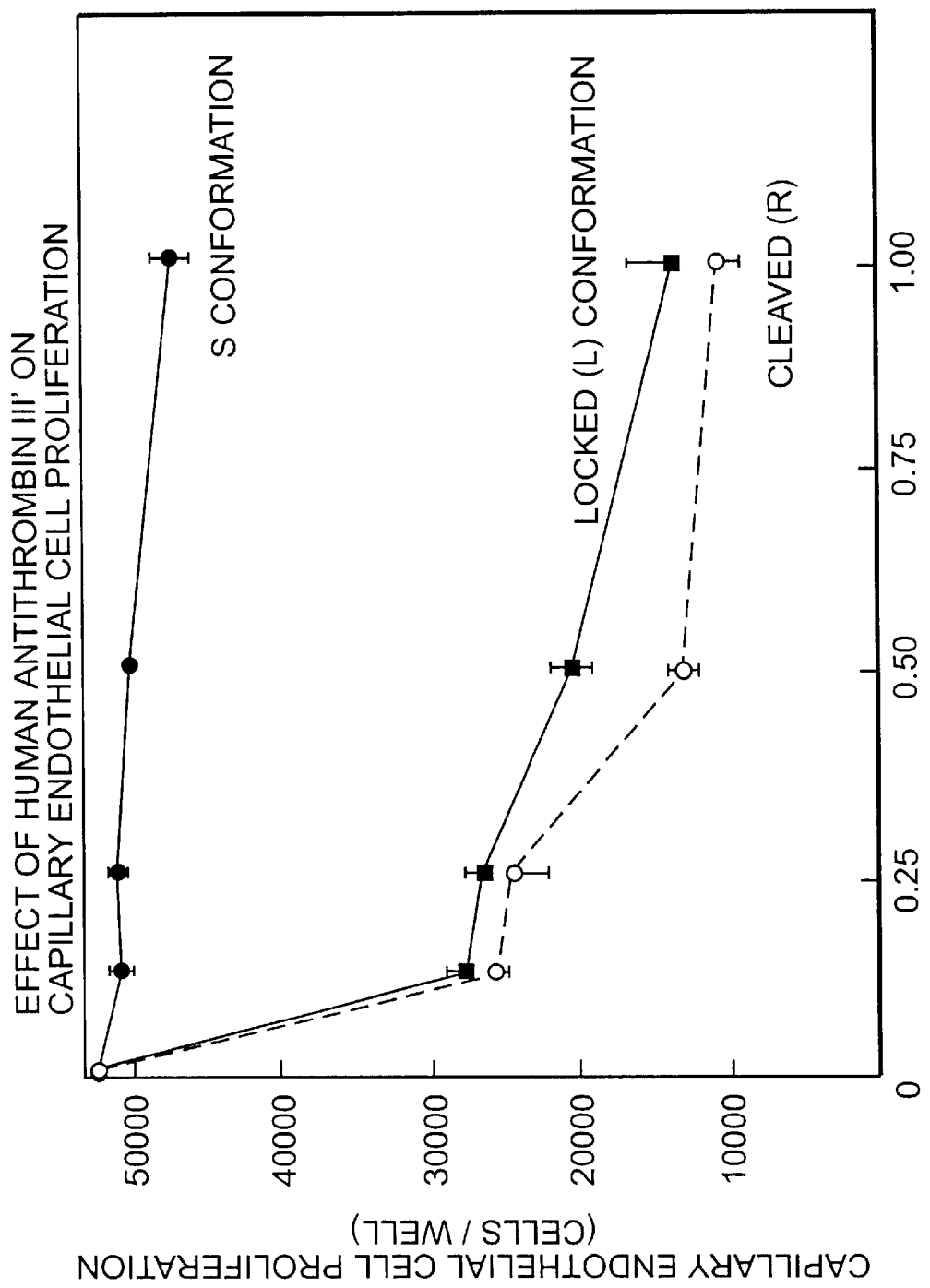

Purified intact bovine and human AT3 (S-AT3), R-AT3 and L-AT3 were tested on capillary endothelial cells in a proliferation assay (FIGS. 3 and 4, respectively). The L-AT3 potently inhibited capillary endothelial cell proliferation in a dose dependent and reversible fashion with half maximal inhibition seen at approximately 50 ng/ml for both the bovine and human protein (FIGS. 3 and 4, respectively). The inhibition was comparable for that seen with the cleaved form of AT3 from the H69 conditioned media or from a digestion of the intact protein with pancreatic elastase. The intact native conformation of bovine and human AT3 had no effect on capillary endothelial cell proliferation at comparable doses (FIGS. 3 and 4, respectively) but did show marginal inhibition at doses in excess of 5 µg/ml. It was determined that virtually all of the AT3 was in the cleaved (R) form that inhibited endothelial cell proliferation in a dose dependent fashion (FIGS. 3 and 4). The data demonstrates that the conformational change that occurs after cleavage of the AT3 molecule confers antiangiogenic activity. The term aaAT3 is used to describe the antiangiogenic form of AT3.

Example 4

Inhibition of in vivo Angiogenesis

In order to determine whether the AT3 fragment, R-conformation, or L-conformation could inhibit in vivo angiogenesis, the chick chorioallantoic membrane (CAM) assay was used. CAM Assay Three-day-old, fertilized white Leghorn eggs (Spafas, Norwich, Conn.) were cracked, and embryos with intact yolks were placed in 100×20 mrn petri dishes. After three days of incubation (37° C. and 3%$CO_2$), a methylcellulose disc containing AT3 was applied to the CAM of individual embryos. The discs were made by desiccation of AT3 in 10 µl of 0.45% methylcellulose on teflon rods. After 48 hours of incubation, embryos and CAMs were observed by means of a stereornicroscope. Embryos were observed daily until there was no evidence of inhibitory zones.

Intact native AT3 had no effect on angiogenesis in the assay but did cause local bleeding at the injection site at higher doses. In contrast, both the R- and L forms of human and bovine AT3 potently inhibited angiogenesis at doses of 20 µg per CAM without evidence of bleeding. In all embryos tested with two separate batches of AT3, there was a potent and sustained inhibition of angiogenesis. No hemorrhage was seen in any of the treated groups, consistent with prior reports that demonstrate these conformations do not bind or inhibit thrombin. There was no evidence of any toxic or inflammatory reaction from any of the proteins tested in the assay at any dose.

Example 5

Inhibition of Tumor Growth
Treatment of Human Malignant Neuroblastoma

Male 6–8 week old C57BI6/J (Jackson Labs, Bar Harbor, Me.) or SCID (MGH) mice were used. Mice were acclimated, caged in groups of 4 or less, their backs shaved, and fed a diet of animal chow and water ad libitum. Methoxyfurane by inhalation was used for anesthesia and euthanasia.

Immunocompromised SCID mice were implanted with human neuroblastorna cells and tumors were allowed to grow to 1% of body weight. This tumor line (SK-NAS) has a consistent pattern of growth. Tumors were measured with a dial caliper, volumes determined using the formula width 2×length×0.52, and the ratio of the treated-to-control volume was determined for the last time point. When tumor volume reached 179–200 mm$^3$, mice were randomized into groups and treated with bovine cleaved AT3 (R) form or the cleaved (R), locked (L) or native intact (S) conformations of human AT3 or vehicle control injected into the subcutaneous flanks once daily at a site distant from the tumor at a dose of 25 mg/kg (500 µg per 20 gram mouse). The experiment was terminated and mice sacrificed and autopsied when control mice began to die or experience significant morbidity.

Figure 5A:
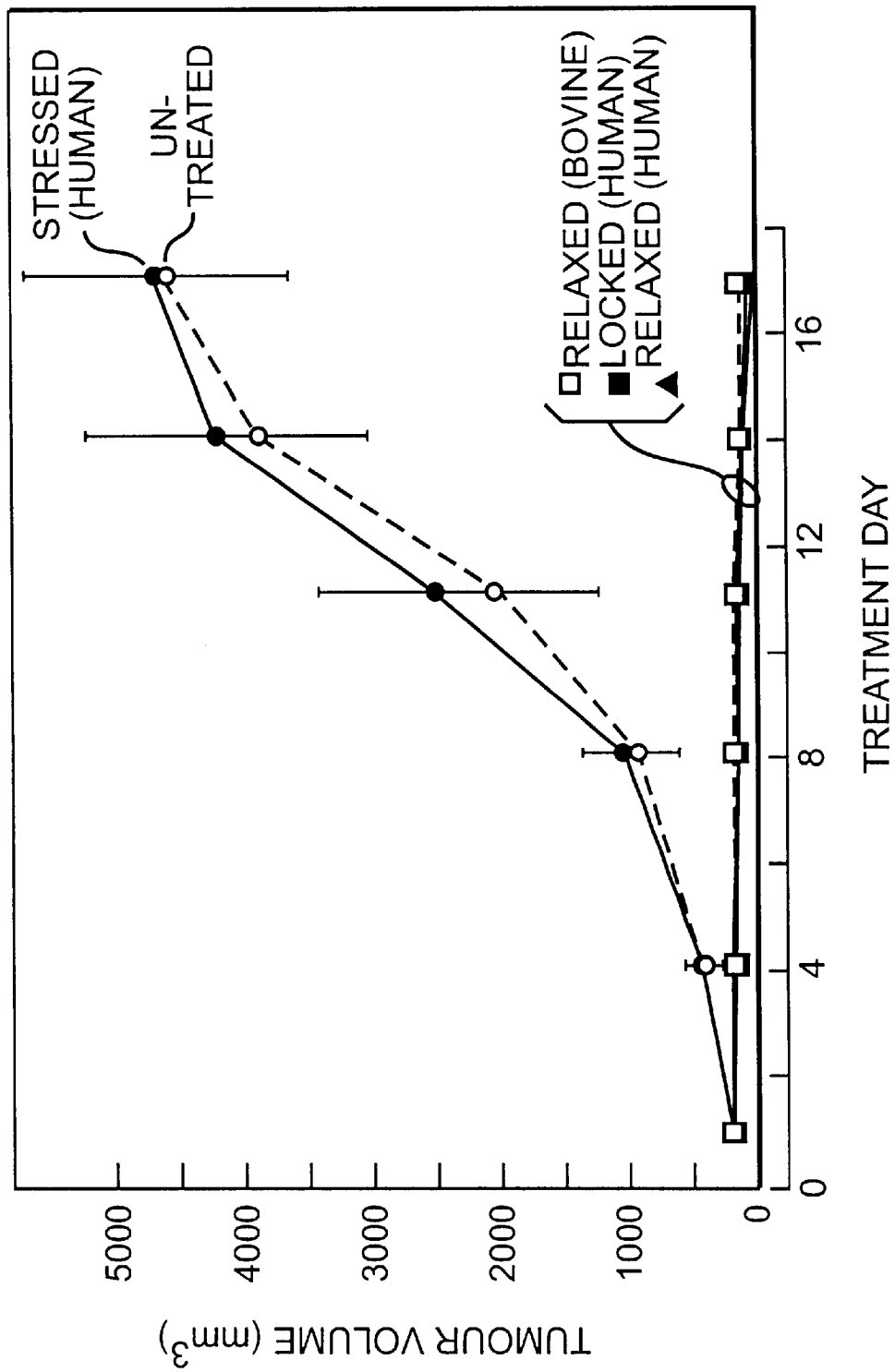
Figure 5B:
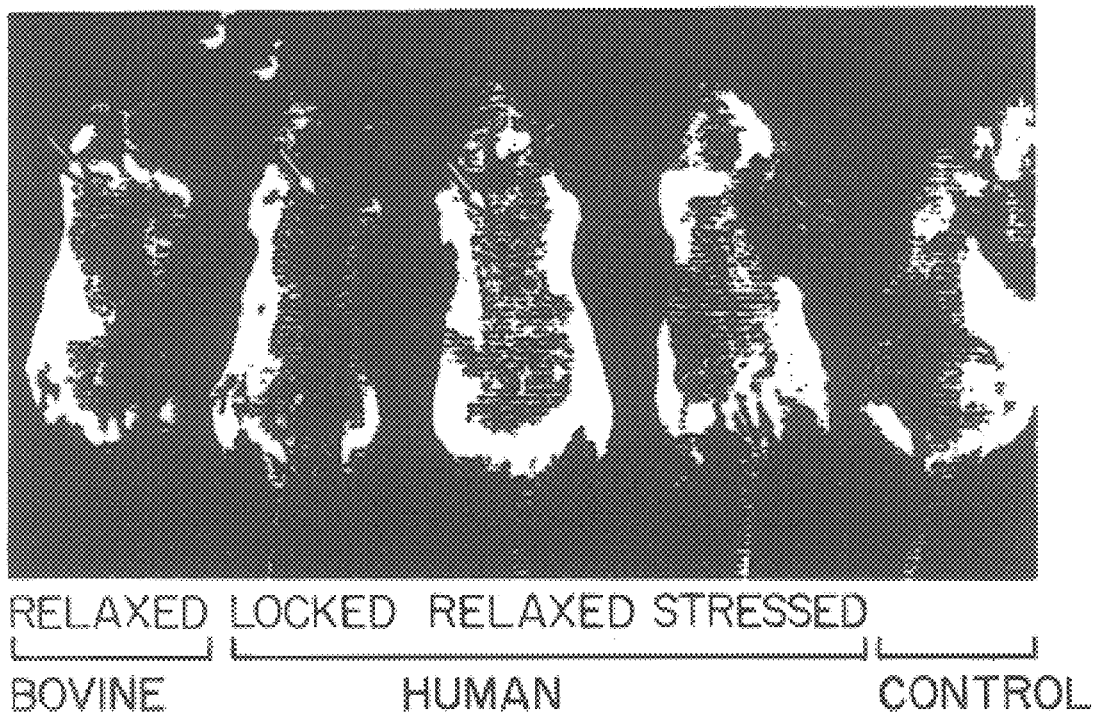

The intact native form of AT3 had no effect on tumor growth as compared to control mice treated with vehicle alone (FIG. 5). In contrast, mice treated with the R- and L-conformation of AT3 had a complete regression of the implanted neuroblastoma; tumors in these mice persisted as small barely visible subcutaneous nodules (FIG. 5). No toxicity was seen in any of the treated mice except for some local bleeding at the injection site of the mice treated with the native intact AT3.

Figure 6:
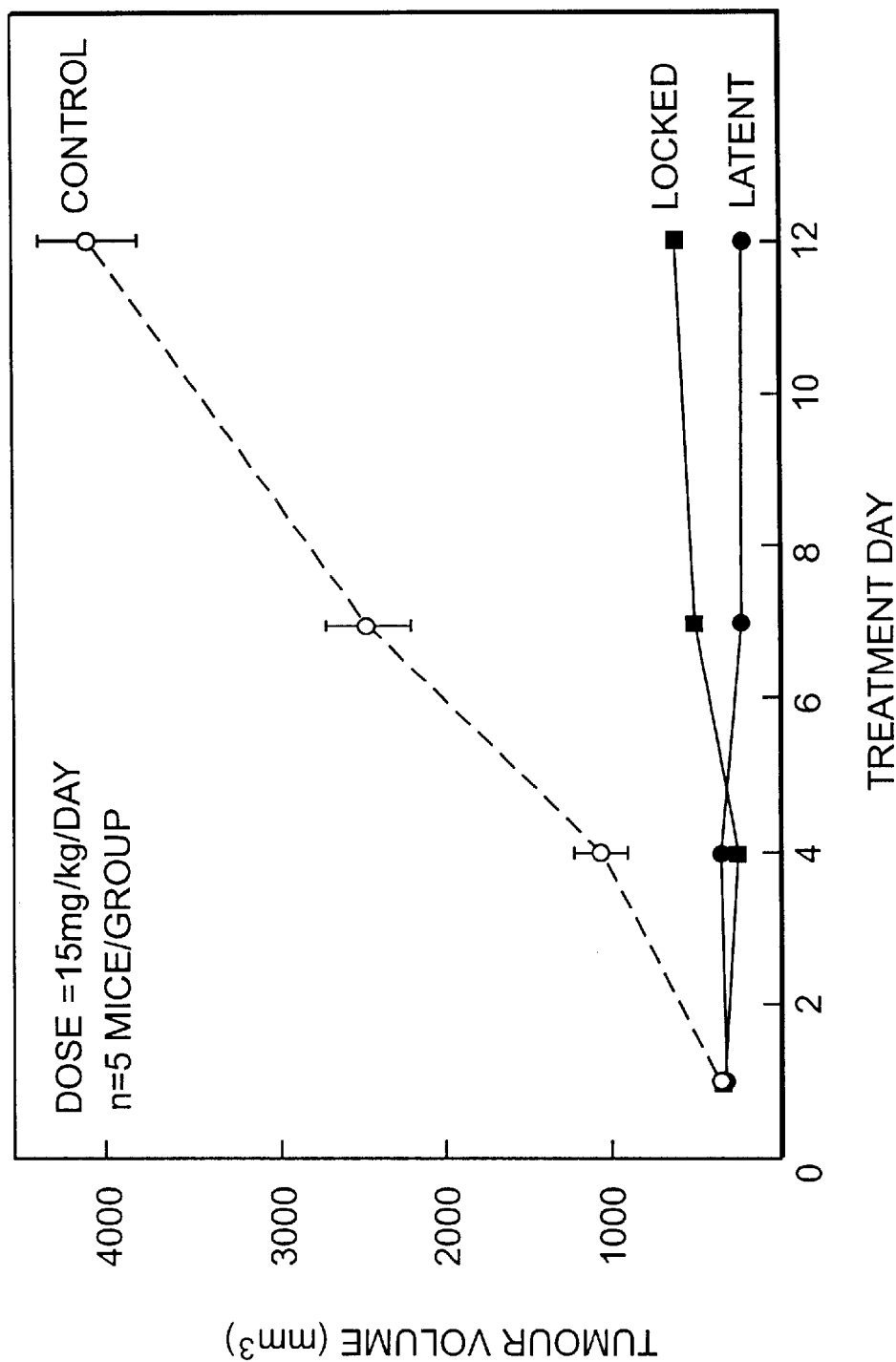

In a separate experiment, SCID mice implanted with human neuroblastoma were treated with latent or locked human AT3 at a dose of 15 mg/kg/day (FIG. 6) and both potently inhibited tumor growth. These data show that aaAT3 is a potent inhibitor of angiogenesis and tumor growth.

Example 6

Method of Identifying Inhibitors of Angiogenesis, Endothelial Cell Proliferation, and/or Tumor Growth In order for a carcinoma to expand beyond a microscopic prevascular state, it must produce stimulators of angiogenesis in excess of inhibitors and must sustain this imbalance. It has been demonstrated that the continued production of angiogenesis inhibitors provides a mechanism for the inhibition of tumor growth by tumor mass. Using murine models of concomitant resistance, angiostatin from a murine lung carcinoma and endostatin from a murine hemangioendothelioma were identified. To determine if human tumors might also produce inhibitors of angiogenesis, human small cell lung cancer was screened for the ability of a primary tumor on the flank of an immunocompromised mouse to inhibit the growth of a similar implant on the opposite flank. Small cell lung cancer was chosen because, clinically, metastatic small cell lung cancer often grows rapidly after definitive treatment of the primary disease.

The phenomenon of the rapid growth of metastasis has been referred to as concomitant immunity, which could be due to the production of an inhibitor of angiogenesis by small cell lung cancer. Several human small cell lung cancer cell lines were screened for the ability of a primary tumor on the flank of an immunocompromised mouse to inhibit the growth of a similar tumor on the opposite flank. One of the tumor lines obtained, a variant of NCI-H69 obtained from the ATCC, which was originally derived from a primary tumor, inhibited a similar tumor by over 80%. By selective in vivo passage, two variants of the H69 line were developed (H69i and H69ni). A tumor model was developed using H69i in which the inhibition of one tumor by another was virtually 100% (line H69i) [FIG. 7A]. A second variant was also developed in which one tumor did not inhibit the other to a significant degree (H69ni) [FIG. 7B].

Tumor cell lines derived from the inhibitory and non-inhibitory variants of H69 were established in vitro. To screen for evidence of the production of an angiogenesis inhibitor, conditioned media was tested on bovine capillary endothelial cells in a 72-hour proliferation assay. When cells were nearly confluent, conditioned media was collected. Conditioned media from the H69i cells potently and reversibly inhibited capillary endothelial cell proliferation. Conditioned media from the H69ni cell line had no significant inhibitory effect on the endothelial cells. The data demonstrates that the purified inhibitor of endothelial cell proliferation generated by the H69i cells is at least in part responsible for the concomitant resistance observed in the tumor model.

Collection of Conditioned Media and Cell Culture

Human small cell lung carcinoma cell lines were obtained from the ATCC and maintained in culture in DMEM supplemented with 10% heat-inactivated fetal calf serum and 1% glutamine-penicillin-streptomycin in a 37° C. and 10% $CO_2$ incubator. Optimal conditions were developed for conditioned media using the minimal volume of media supplemented with the least amount of serum and the maximal contact time for cell viability. To produce conditioned media, 80 milliliter of DMEM with 2.5% FCS and 1% GPS was added to near confluent cells in 900 cm2 roller bottles. After 96 hours at 37° C. land 10% $CO_2$, media was collected, centrifuged (10,000 rpm for 20 minutes), filtered (0.45 µm), and stored at 4° C. The cells were noted to grow as spheroids, which were loosely adherent to the plastic. Media was collected every 96 hours until the spheroid density expanded beyond the limits of the surface area of the roller bottle.

Purification of Inhibitory Activity from Conditioned Media

DEAE, CM, lysine, and heparin Sepharose, Sephacryl S200 HR gel, and a SynChropak RP-4 C4 reverse-phase column were all prepared according to the manufacturers' recommendations. Pooled conditioned media (3–3.5 liters) was diluted three-fold with 10 mM Tris pH 7 and applied to a CM Sepharose column (5×35 cm) coupled to a DEAE Sepharose column (5×35 cm) after equilibration with 10 mM Tris pH 7. Both columns were washed extensively with 10 mM Tris pH 7 and then uncoupled. Each column was eluted with a step gradient of NaCl in 10 mM Tris pH 7 with 50 mM, 0.2 M, 0.6 M, I M and 2 M steps. The DEAE column was washed extensively with 50 mM NaCl in 10 mM Tris to remove phenol red. Fractions with evidence of protein by A280 for each step were pooled and an aliquot of each was applied to bovine capillary endothelial cells in a 72-hour proliferation assay. The 0.2 M NaCl elution of the DEAE column was found to inhibit capillary endothelial cell proliferation and was diluted 2-fold with 10 mM Tris pH 7.

A heparin Sepharose column (2.5×35 cm) was equilibrated with 0.2 M NaCl 10 mM Tris pH 7 and the inhibitory sample from the DEAE column was applied. The column was washed with phosphate buffered saline. The column was then eluted with a continuous gradient of 0.2–2 M NaCl (550 ml total volume) followed by an additional 250 ml of 2 M NaCl. Fractions were collected and an aliquot of each was tested on capillary endothelial cells. Inhibitory activity was found in fractions eluting at 1–1.2 M NaCl. Fractions that inhibited were pooled and concentrated to 1.5 ml using a NanoSpin 30K centrifugal concentrator.

The concentrated sample was applied to a Sephacryl S200 HR column (1.5×75 cm) which was first equilibrated with PBS. The column was eluted with PBS and an aliquot of each fraction collected was tested on capillary endothelial cells. Fractions with inhibitory activity were pooled and concentrated to 1.5 ml using a NanoSpin centrifugal concentrator.

A SynChropak RP-4 (4.6×100 mm) high performance liquid chromatography (HPLC) column was equilibrated with $H_2O$/0.1% trifluoroacetic acid (TFA) and HPLC-grade reagents (Pierce, Rockford, Ill.) were used. The sample from gel filtration was filtered (0.22 µm) and then applied to the column and the column washed with the equilibration buffer. The column was then eluted with a gradient of acetonitrile in 0.1% TFA at 0.5 ml/min and I ml fractions were collected. An aliquot of each fraction was evaporated by vacuum centrifugation, resuspended in PBS, and applied to capillary endothelial cells. The inhibitory activity was further purified to apparent homogeneity by subsequent cycles on the C4 column.

Fractions containing inhibitory activity evaluated by SDS-PAGE and the activity was associated with a band of apparent reduced molecular weight (Mr) of 55 kDa that copurified with a 58–60 kDa band (FIG. 8b). The inhibitory activity was associated with the 55 kDa band. The 55 kDa band was purified to homogeneity using a C4 reverse phase HPLC column and eluted at 55% acetonitrile in 0.1% trifluoroacetic acid (FIG. 8a).

The inhibitory fraction from the final HPLC run was analyzed by microsequence analysis. Protein Microsequencing The 55 kDa (reduced) inhibitor of capillary endothelial cell proliferation was purified to homogeneity from batches of conditioned media. After the final HPLC, a sample containing a single 55 kDa band after staining with silver was used for N-terminal sequence analysis. The N-terminal sequence was determined by automated Edman degradation on a PE/ABD Model 470A protein sequencer (Foster City, Calif.) operated with gas-phase delivery of trifluoroacetic acid. Sequence library searches and alignments were performed against combined GenBank, Brookhaven Protein, SWISS-PROT, and PIR databases. Searches were performed at the National Center for Biotechnology Information through the use of the BLAST network service.

Sequence analysis revealed identity to bovine AT3 (FIG. 2). Mass spectroscopy was performed and revealed a molecular weight of 50 kd. These data identified the inhibitor of angiogenesis as the cleaved form (R-conformation) of bovine AT3 (FIG. 2). SDS-PAGE behavior is also data which tends to confirm the R confirmation. The cleavage site between $Ser_{386}$ and $Thre_{387}$ for bovine AT3 has not previously been described and suggests that a novel enzyme may be involved. Other enzymes that cleave AT3 include thrombin ($Arg_{394}$-$Ser_{395}$), pancreatic elastase ($Val_{388}$-$Iso_{389}$), human neutrophil elastase ($Iso_{391}$-$Ala_{392}$), and a number of others known in the art.

Example 7

Purification of Bovine aaT3 from BxPC3 Conditioned Media

BxPC3 conditioned media (5% FCS) was applied to heparin-Sepharose column, previously equilibrated with 50 mM Tris-HCl, pH 7.4. The column was washed with 2–3 column volumes, and protein was eluted with incremental 0.5M NaCl steps (3 column volumes). Fractions were assayed for the ability to inhibit the proliferation of endothelial cells using well established assay techniques. The fraction eluting from heparin-Sepharose between 1–1.5M NaCl contained a 58 kDa protein that inhibited endothelial cell proliferation. This fraction was concentrated by membrane filtration and applied to a Superdex200 gel filtration column. Fractions were assayed for the ability to inhibit endothelial cell proliferation, and a fraction containing a 58 kDa protein was identified. Sequence analysis of this single band determined it to be bovine antithrombin. Subsequent biochemcial analysis indicated that this AT molecule, with anti-endothelial function, was in fact a "latent" form of bovine AT produced specifically by the BxPC3 cells. This molecule inhibits the proliferation and migration of endothelial cells in a dose dependent manner.

While this invention has been particularly shown and described with references to preferred embodiments thereof, it will be understood by those skilled in the art that various changes in form and details may be made therein without departing from the spirit and scope of the invention as defined by the appended claims.

We claim:

1. A method of reducing tumor growth in a mammal comprising administering to said mammal a composition comprising at least one non native conformation of anti-thrombin III,
   wherein said non native conformation of antithrombin III reduces tumor growth; and
   wherein said non native conformation comprises the N-terminal half of the reactive center loop, or a portion thereof, inserted as a sixth strand into the A-beta sheet of antithrombin III.

2. A method of reducing tumor growth in a mammal according to claim 1 wherein said composition further comprises a physiologically acceptable vehicle.

3. A method of reducing tumor growth in a mammal according to claim 1 wherein said, non-native conformation of antithrombin III is chosen from a synthesized non-native conformation of antithrombin III that reduces endothelial cell proliferation,
   an aggregate of a non-native conformation of antithrombin III that reduces endothelial cell proliferation, and
   a fusion protein of a non-native conformation of antithrombin III that reduces endothelial cell proliferation.

4. A method of reducing tumor growth in a mammal according to claim 1 wherein said non-native conformation of antithrombin III is produced transgenically, recombinantly, or purified from mammal antithrombin III.

5. A method according to claim 1 wherein the N-terminal half of the reactive center loop, or a portion thereof, of an antithrombin III molecule is inserted into the A-beta sheet of the same antithrombin III molecule.

6. A method according to claim 1 wherein the N-terminal half of the reactive center loop, or a portion thereof, of an antithrombin III molecule is inserted into the A-beta sheet of a different antithrombin III molecule.

7. A method of reducing tumor growth in a mammal comprising administering to said mammal a composition comprising at least one non native conformation of antithrombin III,
   wherein said non native conformation of antithrombin III is chosen from the L form of antithrombin III and the R form of antithrombin III.

* * * * *